US008699132B2

(12) United States Patent
Iketaki

(10) Patent No.: US 8,699,132 B2
(45) Date of Patent: Apr. 15, 2014

(54) ULTRA-HIGH RESOLUTION MICROSCOPE

(75) Inventor: Yoshinori Iketaki, Oume (JP)

(73) Assignee: Olympus Corporation, Tokyo (JP)

( * ) Notice: Subject to any disclaimer, the term of this patent is extended or adjusted under 35 U.S.C. 154(b) by 301 days.

(21) Appl. No.: 13/162,993

(22) Filed: Jun. 17, 2011

(65) Prior Publication Data

US 2011/0310475 A1 Dec. 22, 2011

(30) Foreign Application Priority Data

Jun. 17, 2010 (JP) ................................ 2010-138096
Oct. 7, 2010 (JP) ................................ 2010-227698
Mar. 17, 2011 (JP) ................................ 2011-059176

(51) Int. Cl.
*G02B 21/06* (2006.01)

(52) U.S. Cl.
USPC .......................................................... 359/385

(58) Field of Classification Search
USPC ................................................. 359/385–390
See application file for complete search history.

(56) References Cited

U.S. PATENT DOCUMENTS 5,731,588 A 3/1998 Hell et al.
5,777,342 A 7/1998 Baer
5,866,911 A 2/1999 Baer
6,667,830 B1 12/2003 Iketaki et al.
6,859,313 B2 * 2/2005 Iketaki et al. ................ 359/385
7,095,556 B2 * 8/2006 Iketaki et al. ................ 359/385
7,282,716 B2 * 10/2007 Prelewitz et al. ........ 250/370.08
7,470,903 B2 * 12/2008 Prelewitz et al. ............ 250/332
7,848,017 B2 * 12/2010 Ouchi et al. .................. 359/385
7,884,337 B2 * 2/2011 Hasegawa et al. ......... 250/458.1
8,174,761 B2 * 5/2012 Amberger et al. ............ 359/368
2007/0183029 A1 * 8/2007 Iketaki .......................... 359/385
2010/0014156 A1 * 1/2010 Iketaki .......................... 359/385
2010/0214404 A1 * 8/2010 Chen et al. ...................... 348/79
2013/0010353 A1 * 1/2013 Berman ........................ 359/385

FOREIGN PATENT DOCUMENTS

DE 19980759 10/2001
JP B-3020453 1/2000
JP B-3164989 3/2001
JP A-2001-100102 4/2001
JP 2006058477 A * 3/2006
JP A-2010-015026 1/2010

OTHER PUBLICATIONS

Abstract of Japanese Patent Publication No. 08-184552, dated Jul. 16, 1996.
Abstract of Japanese Patent Publication No. 10-142151, dated May 29, 1998.

* cited by examiner

*Primary Examiner* — Frank Font
(74) *Attorney, Agent, or Firm* — Scully, Scott, Murphy & Presser, P.C.

(57) ABSTRACT

A microscope capable of forming a beam spot in a desired shape on a focal plane is provided.
The microscope is provided with a modulation optical element (38) having a plurality of regions for spatial modulation of illumination light and an adjustment element (37) for adjusting an optical property of the illumination light modulated by the modulation optical element.

17 Claims, 24 Drawing Sheets

44 43 spectroscope 39 40 42 41 38 37 32 36 35 erasing light source AOM 34 pumping light source AOM 31 33 laser beam source
laser beam source
laser beam source
laser beam source
laser beam source
71
72
73
74
75
80
81
82
83
84
85
86
87
88
89
90
91
92
93
94
34
60
61
62
37
38
39
95
96
44
97
BPF1
BPF2
BPF3
BPF4
pupil conjugate plane
63
64
40
42
41

(a)
LF1
101 (102)
LF2
LF5
LF4
LF3
(b)
transmittance (%)
λ1
λ2
λ3
λ4
λ5
LF1
LF2
LF3
LF4
LF5
wavelength (nm)

(a)
raw image
Intensty [arb. units]
Distance [arb. units]
(b)
confocal
(airy disc size)
Intensty [arb. units]
Distance [arb. units]
(c)
(ultra-high resolution only)
Intensty [arb. units]
Distance [arb. units]
(d)
confocal + ultra-high resolution
(half width of ultra-high resolution PSF)
Intensty [arb. units]
Distance [arb. units]
0
0.2
0.4
0.6
0.8
1
1.2
0
100
200
300
400
500
600

(a)

(b)

(a)

(b)

PRIOR ART

PRIOR ART

ULTRA-HIGH RESOLUTION MICROSCOPE

CROSS-REFERENCE TO RELATED APPLICATION

The present application claims priority from Japanese Application No. 2010-138096, filed on Jun. 17, 2010, No. 2010-227698, filed on Oct. 7, 2010, and No. 2011-059176, filed on Mar. 17, 2011, the content of which is incorporated herein by reference.

TECHNICAL FIELD

The present invention relates to microscopes.

BACKGROUND ART

An art of optical microscopes is old-established and a variety of types of the microscopes have been developed. In addition, with progress of peripheral technologies including a laser technology and an electronic imaging technology, an even more advanced microscope system has been developed in recent years.

On such a background, there is suggested a highly functional microscope which enables not only a control of contrasts of obtained images but also a scientific analysis thereof by illuminating a sample with multi-wavelength lights to induce double resonance absorption process (for example, see Japanese Patent Laid-Open No. 8-184552).

Such a microscope allows for an observation of absorption and fluorescence caused by a specific optical transition by selecting a specific molecule with the double resonance absorption. A principle thereof will be described with reference to FIG. 19 to FIG. 22. FIG. 19 shows an electronic structure of a valence electron orbital of a molecule composing a sample. First, electrons on the valence electron orbital of the molecule in a ground state (S0 state: stable state) shown in FIG. 19 are excited by light of a wavelength λ1, in order to transit it to a first excited state (S1 state). Next, the electrons are excited by light of a wavelength λ2 in a similar manner, in order to transit it to a second excited state (S2 state) shown in FIG. 21. In this excited state, the molecule emits fluorescence or phosphorescence and returns to the ground state as shown in FIG. 22.

Microscopy adopting the double resonance absorption process is for observing absorption images and emission images by using an absorption process in FIG. 21 and light emission of such as fluorescence and phosphorescence. According to this microscopy, first, the molecule composing the sample is excited to the S1 state by laser light or the like of a resonant wavelength λ1, as shown in FIG. 20. At this time, the number of molecules in the S1 state in a unit cubic volume increases in proportion to an intensity of the light emitted.

Here, a linear absorption coefficient is obtained by multiplying an absorption cross-section per molecule by the number of molecules in the unit cubic volume. Therefore, in an excitation process as shown in FIG. 21, the linear absorption coefficient to light of the resonant wavelength λ2 irradiated subsequently depends on an intensity of the light of the resonant wavelength λ1 initially irradiated. That is, the linear absorption coefficient λ2 to the wavelength λ2 can be controlled by the intensity of the light of the resonant wavelength λ1. This indicates that, by illuminating the sample with the light of the wavelength λ1 and the light of the wavelength λ2 and taking a transmission image by the wavelength λ2, it is possible to control contrasts of the transmission image completely by the light of the wavelength λ1.

In addition, if it is possible to carry out a deexcitation process from the excited state in FIG. 21 to the ground state in FIG. 22 by using fluorescence or phosphorescence, a emission intensity thereof is proportional to the number of molecules in the S1 state. Accordingly, it is possible to control the contrast of the image in using the microscope as a fluorescence microscope, too.

Moreover, the microscopy adopting the double resonance absorption process can perform not only control of contrasts of images as stated above but also chemical analysis. That is, since an orbital of an outermost electron shown in FIG. 19 has an energy level specific to each molecule, the wavelength λ1 is varied among the molecules and, simultaneously, the wavelength λ2 is also specific to the molecules.

Here, even if the sample is irradiated by conventional light of a single wavelength, it is possible, to some degrees, to observe an absorption image or a fluorescent image of particular molecules. Generally, however, since wavelength ranges of absorption bands of some molecules overlap one another, it is not possible to precisely identify a chemical composition of a sample when the sample is irradiated by the light of the single wavelength.

In contrast, the microscopy adopting the double resonance absorption process limits molecules to absorb or to emit light by using two wavelength, λ1 and λ2, which enables more precise identification of the chemical composition of the sample than conventional methods. In addition, in excitation of the valence electron only the light with a particular electric field vector relative to a molecular axis is intensely absorbed, therefore taking the absorption image or the fluorescence image by deciding a polarization direction of the light of the wavelength λ1 and the light of the wavelength λ2 enables identification of orientation directions of the same molecules.

Additionally, there is recently suggested a fluorescence microscope highly capable of a spatial resolution exceeding a diffraction limit by adopting the double resonance absorption process (for example, see Japanese Patent Laid-Open No. 2001-100102).

FIG. 23 shows a conceptual diagram of the double resonance absorption process of the molecule, in which the molecule in the ground state S0 is excited by the light of the wavelength λ1 to the first excited state and further excited by the light of the wavelength λ2 to the second excited state S2. It is to be noted that FIG. 23 shows that fluorescence from a molecule of a certain type in the S2 state is extremely weak.

The molecule with an optical property as shown in FIG. 23 presents a very interesting phenomenon. Like FIG. 23, FIG. 24 is also a conceptual diagram of the double resonance absorption process which shows a vertical axis X representing an expansion of a spatial distance, a spatial area A1 irradiated by the light of the wavelength λ2, and a spatial area A0 not irradiated by the light of the wavelength λ2.

In FIG. 24, numerous molecules in the S1 state are generated by excitation with the light of the wavelength λ1 in the spatial area A0 and, at that time, fluorescence from the spatial area A0 emitted by the light of a wavelength λ3 may be observed. However, since the light of the wavelength λ2 is irradiated to the spatial area A1, most of the molecules in the first excited state S1 are immediately excited to a higher state, the second excited state S2, leaving no molecules in the first excited state S1. This phenomenon is identified for some molecules. Because of this phenomenon, since fluorescence of the wavelength λ3 is completely eliminated in the spatial area A1 and there is no fluorescence from the second excited state S2 from the beginning, fluorescence itself is completely suppressed (fluorescence suppression effect) in the spatial area A1 and fluorescence only from the spatial area A0 is emitted.

In addition, when the light of the wavelength λ2 overlaps a fluorescence emission band, the molecule is forced to transit from the first excited state S1 to a higher vibration level of the ground state S0 by induced emission process. Thus, the fluorescence suppression effect is more enhanced. In other words, with emission of the light of the wavelength λ2, a fluorescence yield emitted from the first excited state S1 is reduced. Accordingly, the fluorescence suppression effect is presented if the molecule is forced to transit to a quantum level. Materials having such properties are photochromic molecules, fluorescent substances including rare earth, quantum dots and the like.

Such a phenomenon has a very important meaning from a point of view of an application field of the microscope. That is, conventional scanning microscopes and the like condense laser beam into a microbeam by using a collective lens in order to scan on the sample to be observed. At this time, a size of the microbeam falls to a diffraction limit dependent on the numerical aperture of the collective lens and the wavelength. Therefore, further spatial resolution cannot be expected in principle.

In a case shown in FIG. 24, however, since the fluorescence area is controlled by spatially partially overlapped two different light of the wavelength λ1 and the light of the wavelength λ2, it is possible, when focusing attention on the emission area of the light of the wavelength λ1, for example, to have the fluorescence area narrower than the diffraction limit depending on the numerical aperture of the collective lens and the wavelength, which leads to a substantial improvement in the spatial resolution. Accordingly, by taking advantage of such a principle, it is possible to substantialize an ultra-high resolution microscope adopting the double resonant absorption process exceeding the diffraction-limited resolution, that is, an ultra-high resolution fluorescence microscope, for example.

In using rhodamine 6G, for example, if light of a wavelength 532 nm (pumping light; first illumination light) is emitted, rhodamine 6G molecules are excited from the ground state S0 to the first excited state S1 and emit fluorescence with a peak at a wavelength of 560 nm. At this time, if light of a wavelength 599 nm (erasing light; second illumination light) is irradiated it causes the double resonance absorption process, rendering the rhodamine 6G molecules transit to the second excited state, in which fluorescent emission is difficult. More specifically, simultaneous irradiation of the pumping light and erasing light to rhodamine 6G suppresses fluorescence.

FIG. 25 is a main section configuration diagram of the ultra-high resolution microscope conventionally suggested. This ultra-high resolution microscope is based on a usual fluorescence microscope of laser scanning type and comprising three independent units, that is, a light source unit 210, a scanning unit 230 and a microscope unit 250.

The light source unit 210 has a pumping light source 211 and an erasing light source 212. The pumping light emitted from the pumping light source 211 is incident to a dichroic prism 213 and is reflected thereby. The erasing light emitted from the erasing light source 212 is incident to the dichroic prism 213 after being subjected to spatial modulation of its phase by a modulation optical element 215, transmits through the dichroic prism 213 and then exits as combined concentrically with the pumping light.

Here, in observing the sample dyed with rhodamine 6G the pumping light source 211 is configured, using Nd:YAG laser, to emit the light of the wavelength 532 nm, which is second harmonic waves of the laser. In addition, the erasing light source 212 is configured, using Nd:YAG laser and Raman shifter, to emit light, which is second harmonic waves of the Nd:YAG laser modulated into the light of the wavelength 599 nm by the Raman shifter, as the erasing light.

The modulation optical element 215 modulates the phase of the erasing light and has a pupil plane radially divided into 8 regions about an optical axis as shown in FIG. 26, for example. Each of the regions is formed by forming optical multilayer films having phases different by λ/8 of the wavelength of the erasing light from one another such that a phase difference of the erasing light revolves by 2π about the optical axis or by etching a glass substrate. When the erasing light having transmitted through the modulation optical element 215 is collected, it generates a hollow erasing light canceling the electric filed on the optical axis.

The scanning unit 230, after passing the pumping light and the erasing light coaxially emitted from the light source unit 210 through a half prism 231, performs swing scanning in a two-dimensional directions with two galvano mirrors 232, 233 in order to emit the lights to the microscope unit 250, which will be described below. In addition, the scanning unit 230 branches fluorescence incident from the microscope unit 250 tracking back its path by using the half prism 231, such that branched fluorescence is received by a photomultiplier 238 via a projector lens 234, a pinhole 235, and notch filters 236, 237.

For the sake of simplification of the diagram, the galvano mirrors 232, 233 are swingable in a coplanar manner in FIG. 25. The notch filters 236, 237 eliminate the pumping light and the erasing light mixed into fluorescence. In addition, the pinhole 235 is an important optical element composing a confocal optical system and passes only fluorescence emitted on a particular cross-section in the sample being observed.

The microscope unit 250 is a usual fluorescence microscope which reflects the pumping light and the erasing light incident from the scanning unit 230 on the half prism 251 and collects the lights, by using a microscope objective lens 252, on a sample to be observed containing molecules with three electron states including at least the ground state. In addition, fluorescence emitted on a sample 253 is collimated by the objective lens 252 again and reflected on the half prism 251 so as to return to the scanning unit 230, while a part of fluorescence passing the half prism 251 is led to an eyepiece 254 so as to be visually observed as a fluorescence image.

According to this ultra-high resolution microscope, fluorescence except the same close to the optical axis, at which the intensity of the erasing light becomes zero on a focusing point of the sample 253, is controlled and, as a result, it enables to measure only fluorescence labeler molecules in a region narrower than a width of the pumping light. Accordingly, by arranging fluorescent signals at each measurement point in the two-dimension on a computer, it is possible to form a microscopic image having a resolution exceeding the spatial resolution of the diffraction limit.

It is to be noted that the modulation optical element may be configured to modulate polarization of the erasing light in order to generate a hollow erasing light canceling the electric field on the optical axis (for example, see Y. Iketaki, et. al, Rev. Sci. Instrum. 75 (2004)5131). In addition, the modulation optical element may be disposed on a common optical path of the pumping light and the erasing light (for example, see Japanese Patent Laid-Open No. 2010-15026). In this case, the modulation optical element is formed into an annular shape having a center region and a peripheral region separated concentrically. The center region has optical multilayer formed on a transparent optical substrate, such as a glass substrate or the like, to reflect the pumping light while making the erasing light transmit therethrough by inverting the phase by $\pi$. The peripheral region is formed of an optical substrate, for example, and makes the pumping light and the erasing light transmit therethrough without phase modulation. Alternatively, the modulation optical element has a plurality of regions radially divided about the optical axis, each of which is formed of the optical multilayer for making the pumping light transmit in the same phase while modulating the phase of the erasing light in order to form a Laguerre-Gaussian beam with a phase distribution revolving by $2\pi$.

SUMMARY OF THE INVENTION

A microscope according to a first aspect of the present invention includes:

a modulation optical element having a plurality of regions for spatially modulating illumination light; and an adjustment element for adjusting an optical property of the illumination light modulated by the modulation optical element.

A second aspect of the present invention is the microscope according to the first aspect, wherein the adjustment element adjusts the illumination light having passed though the modulation optical element such that an unsymmetrical component of at least one of a transmittance and a phase around an optical axis is cancelled out between the plurality of regions of the modulation optical element.

A third aspect of the present invention is the microscope according to the first aspect, wherein the adjustment element adjusts such that the following relation expression is satisfied, provided that $S_i$ represents dimensions of each region i corresponding to the plurality of regions on a pupil plane of the illumination light spatially modulated by the modulation optical element, $\theta_i$ represents a phase of a light having passed through the area i, $T_i$ represents the transmittance, and $U_i$ represents an energy density.

$$\sum_{i=1}^{n} T_i S_i \sin\theta_i = \sum_{i=1}^{n} U_i = 0 \quad \text{[Formula 1]}$$

A fourth aspect of the present invention is the microscope according to the first aspect, wherein the adjustment element is integrally formed in the modulation optical element.

A fifth aspect of the present invention is the microscope according to the first aspect, wherein the modulation optical element includes regions radially divided about the optical axis as the plurality of areas.

A sixth aspect of the present invention is the microscope according to the fifth aspect, wherein the following equation $$T_a S_a \sin\theta_a + T_b S_b \sin\theta_b = 0$$

is satisfied, provided that, for the plurality of regions of the modulation optical element, a region a has a transmittance $T_a$, dimensions $S_a$ and a phase $\theta_a$, whereas a region b, located across the optical axis from the region a, has a transmittance $T_b$, dimensions $S_b$ and a phase $\theta_b$.

A seventh aspect of the present invention is the microscope according to the sixth aspect, wherein the region a and the region b are in the same size.

An eighth aspect of the present invention is the microscope according to the first aspect, wherein the modulation optical element includes concentrically divided regions as the plurality of regions.

A ninth aspect of the present invention is the microscope according to the first aspect, wherein the illumination light has a first illumination light for making a material having at least two excited quantum states emit light by exciting the material from a stable state to a first quantum state, and a second illumination light for suppressing by making the material further transit to another quantum state;

the microscope further comprising an illumination optical system including an objective lens for collecting the first illumination light and the second illumination light on a sample including the material by partially overlapping the lights; and the modulation optical element and the adjustment element are disposed in the illumination optical system.

A tenth aspect of the present invention is the microscope according to the ninth aspect, wherein the modulation optical element modulates a phase of the second illumination light.

An eleventh aspect of the present invention is the microscope according to the tenth aspect, wherein the modulation optical element makes the first illumination light transmit without changing a sign of an electric field.

A twelfth aspect of the present invention is the microscope according to the eleventh aspect, wherein the modulation optical element has optical multilayer.

A thirteenth aspect of the present invention is the base station according to the ninth aspect, wherein the illumination optical system overlaps an optical axis of the first illumination light and an optical axis of the second illumination light in a spatially matching manner.

A fourteenth aspect of the present invention is the microscope according to the thirteenth aspect, wherein the illumination optical system has a single mode fiber, and the first illumination light and the second illumination light are incident on the modulation optical element and the adjustment element via the single mode fiber.

A fifteenth aspect of the present invention is the microscope according to the ninth aspect, wherein the adjustment element comprises an iris for adjusting a diameter of luminous flux of the illumination light.

A sixteenth aspect of the present invention is the microscope according to the fifteenth aspect, wherein the iris is movable in a direction orthogonal to the optical axis of the illumination light entering.

A seventeenth aspect of the present invention is the microscope according to the ninth aspect, comprising a plurality of illumination light sources capable of generating illumination lights of at least three kinds of wavelengths, wherein the first illumination light and the second illumination light are simultaneously generated from the plurality of illumination light sources.

An eighteenth aspect of the present invention is the microscope according to the seventeenth aspect, comprising:

a photodetector for detecting emitted light from the sample as irradiated with the first illumination light and the second illumination light from the illumination optical system;

a confocal pinhole having an aperture of variable size, disposed in a position conjugate with a focal position of the objective lens on an incidence side of the photodetector;

a drive unit for varying the size of the aperture of the confocal pinhole; and a control unit for simultaneously generating the first illumination light and the second illumination light by controlling the plurality of illumination light sources and also for controlling the aperture of the confocal pinhole, via the drive unit, in order to satisfy the following formula in accordance with the first illumination light and the second illumination light.

$$0.61\frac{\lambda_p}{NA}M > a \geq 0.49\sqrt{\frac{\varepsilon_e}{\tau\sigma_{dip}C_{e0}}}\frac{\lambda_e}{NA}M \quad \text{[Formula 2]}$$

NA: numerical aperture of objective lens
M: magnification of photodetector for focusing image on object side
lp: wavelength of first illumination light
le: wavelength of second illumination light
$S_{dip}$: fluorescence suppressing cross-section
$C_{e0}$: peak intensity of second illumination light
$e_e$: photon flux of second illumination light

DESCRIPTION OF EMBODIMENTS

Summary of Invention

First, a summary of the present invention is described by taking, as an example, a super-high resolution microscope of a emission suppression type for achieving super-high resolution by suppressing light emission of a material by adopting a two-color illumination light.

According to an embodiment of the present invention, in an illumination optical system of an erasing light of the super-high resolution microscope, an optical property of the erasing light is adjusted, in order to maintain uniformity of an intensity distribution of the erasing light modulated by the modulation optical element in a pupil plane.

Figure 1:
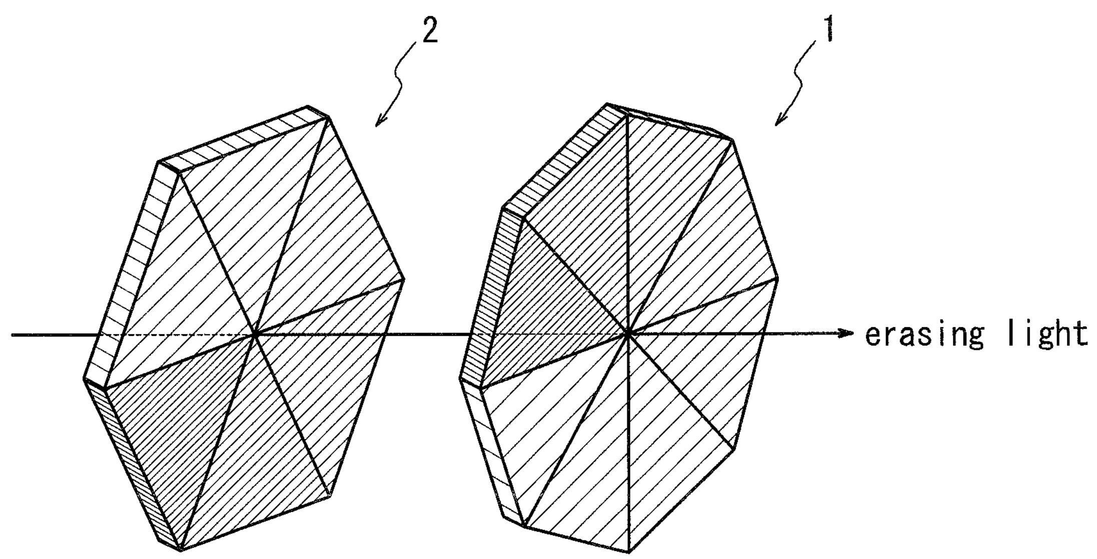
FIG. 1 is a diagram illustrating examples of a modulation optical element and an adjustment element.

As a first efficient countermeasure, an amplitude modulation element is provided for correcting the intensity distribution of the erasing light. FIG. 1 is a diagram illustrating examples of the modulation optical element and the adjustment element. A modulation optical element 1 has a plurality of optical multilayer regions radially divided (into 8 sections in FIG. 1) such that a phase (phase distribution) revolves about an optical axis by 2π relative to the erasing light. The modulation optical element 1 is disposed on an optical path of the erasing light or a common optical path of a pumping light and the erasing light, thereby modulating the phase or polarization of the erasing light.

In using this modulation optical element 1, a transmittance compensation plate 2, which is the adjustment element, is disposed on an incidence plane side or an exit plane side (the incidence plane side in FIG. 1) of the modulation optical element 1, for example. Formed on the transmittance compensation plate 2 are a plurality of transmittance compensation regions formed of an absorption layer of the erasing light radially divided (into 6 sections in FIG. 1) about the optical axis. The absorption layer forming the transmittance compensation regions may be a single layer or multilayer.

Thereby, the transmittance of each of the optical multilayer regions of the modulation optical element 1 is controlled by a corresponding transmittance compensation region of the transmittance compensation plate 2, in order to uniform an amplitude of the erasing light incident on a latter optical element (not shown) from the modulation optical element 1. Alternatively, since each of the optical multilayer regions of the modulation optical element 1 has a lower transmittance in proportion to the number of layers in general, each of the optical multilayer regions on a substrate of the modulation optical element is simultaneously coated with the absorption layer for uniforming the transmittance. In this case, the transmittance compensation plate 2 is integrated in the modulation optical element 1.

As a second effective countermeasure, in comprehensive consideration of the phase modulated by the modulation optical element, such as amplitude and dimensions of a modulation region, an electric field is cancelled out by an interference when the erasing light, having passed through the pupil plane, is focused on a focal point. That is, if the modulation optical element divides the pupil plane of the erasing light into n regions, the following relational expression is satisfied, provided that $S_i$ represents the dimensions of each region i, $\theta_i$, represents the phase, $T_i$ represents the transmittance, and $U_i$ represents an energy density.

[Formula 3]

$$\sum_{i=1}^{n} T_i S_i \sin\theta_i = \sum_{i=1}^{n} U_i = 0 \quad (1)$$

As can be seen in the above relational expression, each of the region i of the modulation optical element has the transmittance $T_i$, the dimensions $S_i$ and the phase $\theta_i$ as design parameters. Accordingly, in comparison to a conventional super-high resolution microscope which assumes that the transmittance of the modulation optical element is 1, the present invention offers better flexibility in designing the microscope. Hence, if the transmittance deteriorates on the optical multilayer of the modulation optical element, for example, it can be adjusted with the dimensions of such area. In addition, if the transmittance deteriorates, it is possible to compensate it with a quantity of a phase change of such region.

Figure 2:
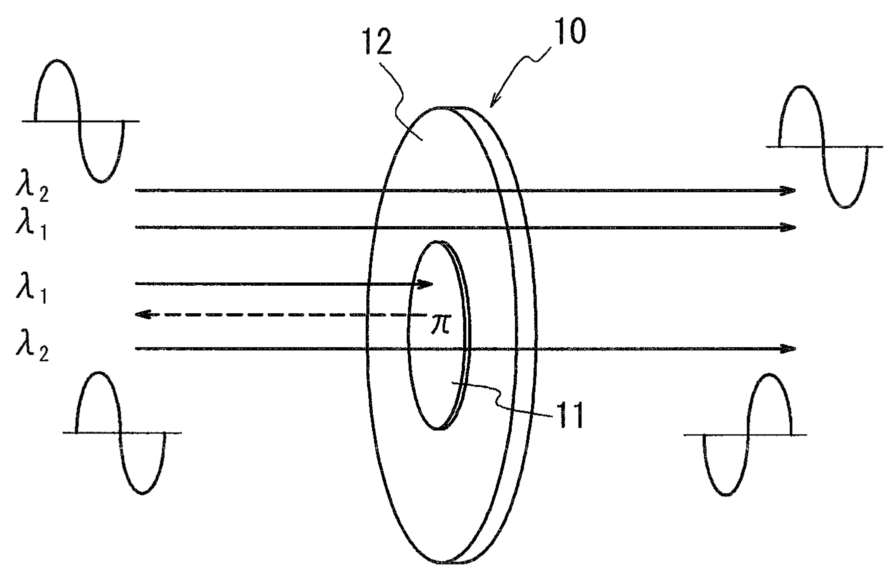
FIG. 2 is a diagram illustrating another example of the modulation optical element.

This countermeasure is effective especially to a modulation optical element 10 shown in FIG. 2. The modulation optical element 10 shown in FIG. 2 is concentrically divided into a center region 11 and a peripheral region 12 both in an annular shape and disposed on the common optical path of the pumping light and the erasing light. The center region 11 is formed of optical multilayer formed on a transparent optical substrate, such as a glass substrate, for reflecting the pumping light of wavelength λ1, while making the erasing light of the wavelength λ2 transmit by reversing the phase by π. The peripheral region 12 is formed of an optical substrate, for example, for transmitting the pumping light and the erasing light without modulating their phases.

In using the modulation optical element 10, the following formula is satisfied. Thereby, when coherent erasing lights having passed through the modulation optical element 10 are overlapped one another, it is possible to make an electric intensity of the erasing light zero on the focal point. In the following formula, $T_a$, $S_a$ and $\theta_a$ represent the transmittance, the dimensions and the phase of the center region 11 respectively, whereas $T_b$, $S_b$ and $\theta_b$ represent the transmittance, the dimension and the phase of the peripheral region 12 respectively.

$$T_a S_a \sin\theta_a + T_b S_b \sin\theta_b = 0 \quad (2)$$

In addition, also in using the modulation optical element 1 radially divided into the plurality of optical multilayer regions about the optical axis as shown in FIG. 1, the above formula (2) is satisfied using $T_a$ and $T_b$, $S_a$ and $S_b$, and $\theta_a$ and $\theta_b$ respectively representing the transmittances, the dimensions and the phases of the optical multilayer regions located across the optical axis from one another. If the modulation optical element 1 shown in FIG. 1 has the optical multilayer regions in the same size located across the optical axis from one another, the following formula (3) is satisfied. Thereby, it is possible to make the electric intensity of the erasing light zero on the focal point in the similar manner as stated above.

$$T_a \sin\theta_a + T_b \sin\theta_b = 0 \quad (3)$$

As stated above, in proportion to the number of design parameters of the modulation optical element, it allows for various and more flexible designs, which increases a permissible level of manufacturing errors in an actual scene. As a result, for example, it allows for a wider selection of a material of the optical multilayer.

In using the super-high resolution microscope of the emission suppression type adopting the two-color illumination light, it is generally extremely difficult to adjust the optical axes of illumination lights in different colors. In this case, that is, there is a necessity for an alignment of the illumination optical system such that the two illumination lights in different colors completely coaxially match each other and also focused on the same focal point without aberration. As a solution for it, it is effective, for example, to make the pumping light and the erasing light simultaneously enter the modulation optical element by concentrically arranging them in advance by using the single mode fiber, and to modulate the phase of only the erasing light by using the modulation optical element so as to form a follow beam, while making the pumping light transmit with the same signs of the electric field, that is, without changing the signs, at least on the pupil plane having the phase distribution to be collected in the normal Gaussian shape.

Figure 25:
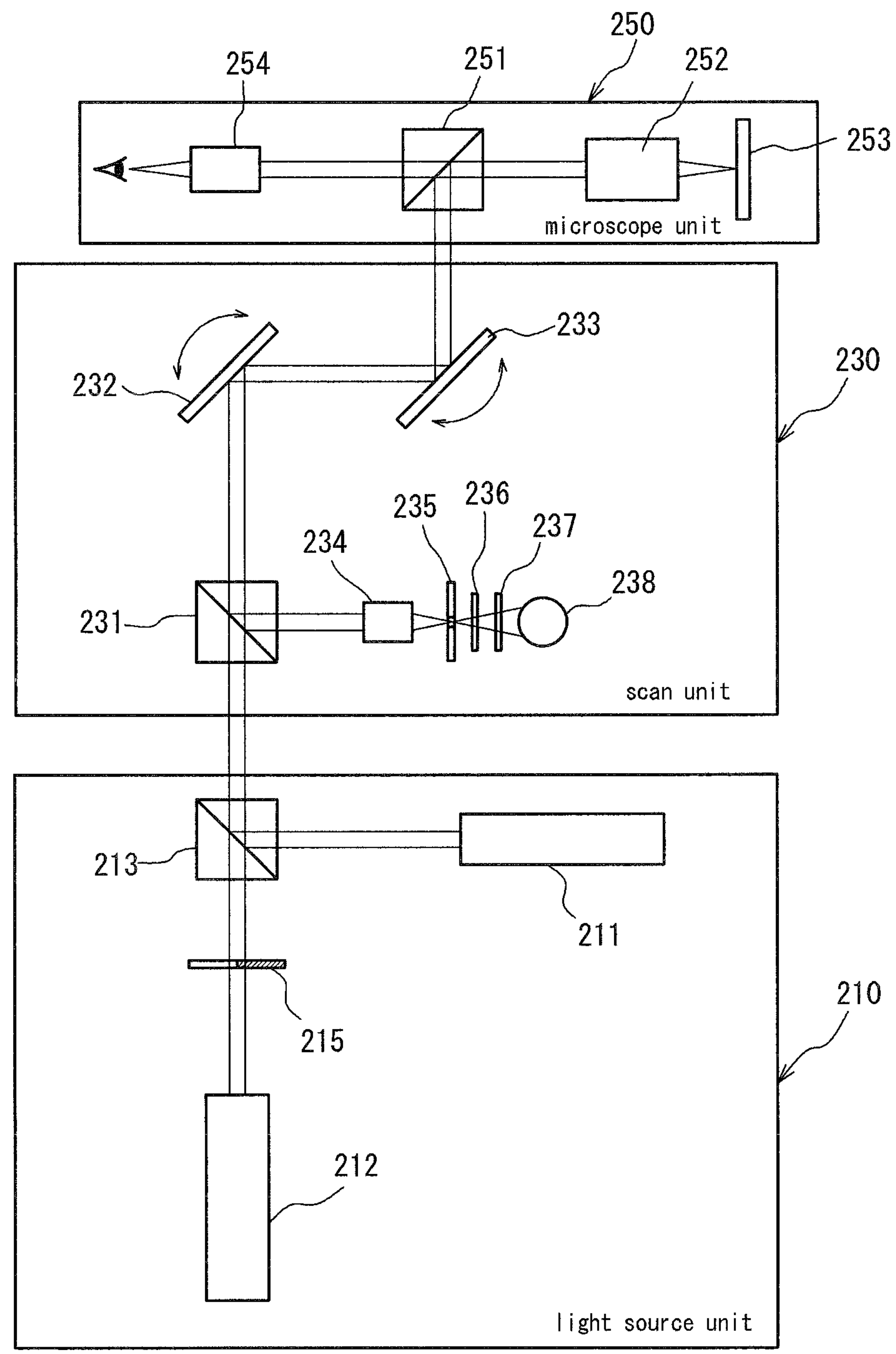
FIG. 25 is a configuration diagram of a main section of a conventional super-high resolution microscope.
Figure 26:
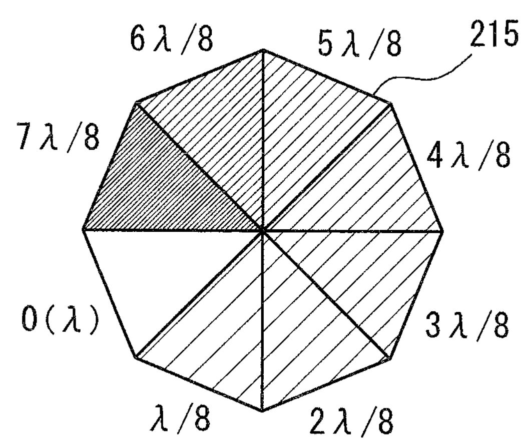
FIG. 26 is an enlarged plan view illustrating a configuration of a phase plate shown in FIG. 25.

Thereby, collection of the pumping light and the erasing light having passed through the modulation optical element enables easy satisfaction of an imaging condition to present an ultra-high resolution function, in comparison to a case in which, as shown in FIG. 25, the erasing light is shaped into the beam and collected together with the pumping light after having an optical axis adjustment therewith. That is, in the case in FIG. 25, since the erasing light is adjusted simultaneously with the pumping light after being shaped into the beam, it requires advanced techniques to adjust a mirror optical system for matching the optical axis but still cannot offer a good stability after an adjustment. In contrast, by concentrically arranging the pumping light and the erasing light with the single mode fiber in advance as stated above and collecting them via the modulation optical element and a light collection optical system, it allows for an easy coaxial arrangement of the pumping light and the erasing light and, moreover, stable collection of the lights without causing an axial offset.

In addition, if the pumping light and the erasing light are coaxially incident on the modulation optical element, the modulation optical element may be manufactured by using the optical multilayer as shown in FIG. 1 or FIG. 2, for example. In this case, if each of the regions has a different transmittance, the formula (1) is highly effective. That is, fluctuation of the transmittance in each of the regions may be easily compensated by using the phase difference of the dimensions. According to the present invention, therefore, in practical use of the microscope using the modulation optical element, it is possible to obtain high flexibility thereof and to easily form the beam spot in a desired shape on the focal plane.

Although the above description is for application of the present invention to the ultra-high resolution microscope of the emission suppression type adopting the two-color light, the present invention is also effectively applicable to a microscope adopting a single-color coherent light. For example, the present invention may be applied to the microscope for forming multi-spot by phase modulation of the one-color light with the modulation optical element, in order to form the multi-spot in a desired shape. Moreover, the present invention may also be applicable to a differential interference microscope for detecting a differential quantity of the phase difference by generating a hollow illumination light, a soft X-ray microscope of a phase difference detection type (for example, see N. Borkor, Opt. Express 17 (2009)5533) and the like, in order to form a spot in a desired shape.

Figure 3:
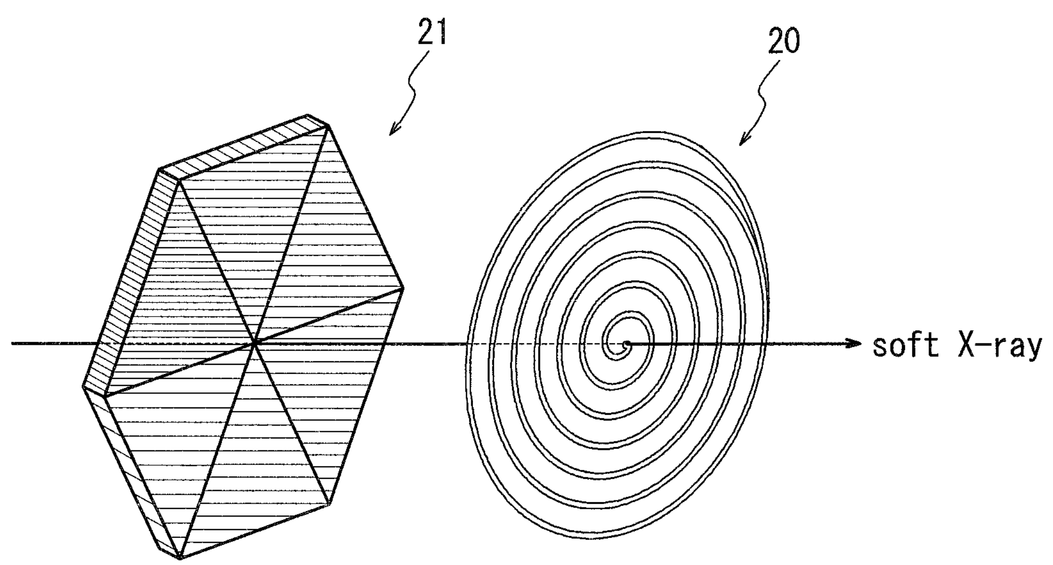
FIG. 3 is a diagram illustrating examples of the modulation optical element and the adjustment element for soft X-ray.

Especially if the present invention is applied to the latter soft X-ray microscope, it is possible, by combining, for example, the modulation optical element formed of a Fresnel zone plate 20 of a spiral type as shown in FIG. 3 and an absorption filter formed of a transmittance compensation plate 21 divided into a plurality of regions about the optical axis as shown in FIG. 1, to compensate the transmittance of the soft X-ray of the Fresnel zone plate 20 and to form a soft X-ray spot in a desired shape.

Embodiments of the present invention will be described with reference to the accompanying drawings.

First Embodiment

Figure 4:
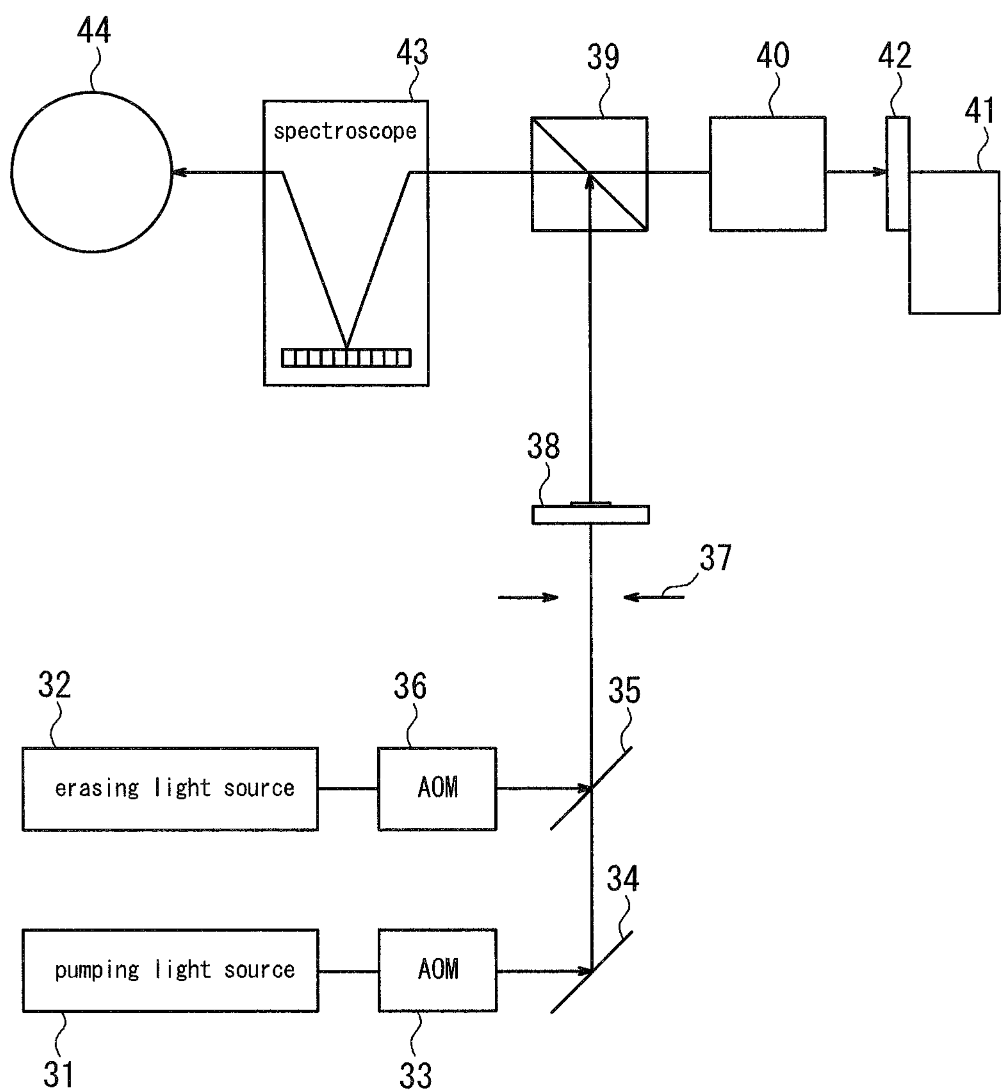
FIG. 4 is a diagram illustrating a schematic configuration of a main section of a super-high resolution microscope according to a first embodiment.

FIG. 4 is a diagram illustrating a schematic configuration of a main section of an ultra-high resolution microscope according to a first embodiment of the present invention. The ultra-high resolution microscope is of the emission suppression type adopting the two-color light and has a pumping light source 31 and an erasing light source 32. The pumping light source 31 has an Nd:YAG laser, for example, and emits second harmonic waves, as the pumping light, having a wavelength 532 nm. Meanwhile, the erasing light source 32 has a krypton laser, for example, and emits light of a wavelength 647 nm as the erasing light.

The pumping light from the pumping light source 31 is modulated its intensity, if necessary, by an AOM (Acousto-Optic Modulator) 33, reflected by a reflector 34 and then transmits a dichroic mirror 35. Meanwhile, the erasing light from the erasing light source 32 is also modulated its intensity, if necessary, by an AOM (Acousto-Optic Modulator) 36, reflected coaxially with the pumping light by the dichroic mirror 35 and then combined with the pumping light.

The pumping light and the erasing light combined with each other by the dichroic mirror 35 is incident on a modulation optical element 38 via an iris 37, which is the adjustment element. The iris 37 is configured to be able to adjust a diameter of luminous flux of the combined pumping light and the erasing light. In addition, the iris 37 is configured to be movable within a plane orthogonal to the optical axis, as necessary. Thereby, the optical axis of the combined pumping light and the erasing light are decentered (optical axis shift).

As shown in FIG. 2, for example, the modulation optical element 38 is configured to have the center region and the peripheral region both in the annular shape. In this case, the center region of the modulation optical element 38 is configured, for example, to have optical multilayer, as shown in the following table, on the optical substrate. In the following table, a first layer and a tenth layer represent the bottom layer and the top layer, respectively. In addition, if uniform erasing light is incident, a diameter of the center region is $1/2^{1/2}$ of a diameter of the pupil of the erasing light from the formula (1). Thereby, it is possible to form a spot pattern in a donut shape on a focal plane of a sample 42 by reversing the phase of the erasing light of the wavelength 647 nm.

TABLE 1

| Designed Film Thickness | | | |
|---|---|---|---|
| Layer | Physical Film Thickness (nm) | Optical Film Thickness (4/λ) | Material |
| First Layer | 157.8 | 1.4 | $S_iO_2$ |
| Second Layer | 205.3 | 3.0 | $T_iO_2$ |
| Third Layer | 162.8 | 1.5 | $S_iO_2$ |
| Fourth Layer | 68.8 | 1.0 | $T_iO_2$ |
| Fifth Layer | 163.0 | 1.5 | $S_iO_2$ |
| Sixth Layer | 59.7 | 0.9 | $T_iO_2$ |
| Seventh Layer | 173.5 | 1.6 | $S_iO_2$ |
| Eighth Layer | 62.8 | 0.9 | $T_iO_2$ |
| Ninth Layer | 148.1 | 1.3 | $S_iO_2$ |
| Tenth Layer | 92.7 | 1.4 | $T_iO_2$ |

| Refractive Index | | |
|---|---|---|
| Wavelength (nm) | $S_iO_2$ | $T_iO_2$ |
| 532 | 1.48 | 2.42 |
| 647 | 1.47 | 2.36 |

The pumping light and the erasing light having passed through the modulation optical element 38 are reflected by a beam splitter 39 and then focused on the sample 42 held on a sample stage 41 by a microscope objective lens 40. Then, the light obtained from the sample 42, after being collected by the microscope objective lens 40 and transmits through the beam splitter 39, dispersed by a spectroscope 43, such that a signal light (fluorescence) of a necessary wavelength element is received by an photodetector 44 composed of a photomultiplier, for example. The sample 42 is spatially scanned as the sample stage 41 moves, thereby a fluorescence image of the sample 42 is generated based on the signal obtained from the photodetector 44.

In such a configuration, the modulation optical element 38, in forming the optical multilayer, may have different designed values of the property of the optical multilayer, such as the phase modulation different from π and the transmittance dramatically lower than 100%. In addition, laser beams of the pumping light and the erasing light generally have non-uniform in-plane intensity but are in the form of Gaussian beams symmetric relative to the optical axis. Therefore, it is assumed that the shape of the spot of the erasing light collected on the sample 42 fails to become symmetric relative to the optical axis but is deformed, resulting in being unable to obtain an expected ultra-high resolution function and deteriorating a quality of the fluorescence image.

The ultra-high resolution microscope according to the present embodiment has the iris 37, as the adjustment element, on an incidence side of the modulation optical element 38. Accordingly, simple operations by the iris 37 to adjust the diameters of the pumping light and the erasing light and to adjust the optical axis (eccentricity) as necessary enables full adjustment of a ratio of the dimensions of the center region having the optical multilayer on the modulation optical element 38 and transmittance dimensions of the peripheral regions for the erasing light. Thereby, it is possible to find out conditions to satisfy the formula (2), which enables easy compensation of the manufacturing errors of the modulation optical element 38, adjusting the optical property of the erasing light modulated by the modulation optical element 38.

In addition, the pumping light is composed coaxially with the erasing light and, without polarity reversal of the electric field, collected in the normal Gaussian shape on the sample 42. Accordingly, if a chromatic aberration of the microscope objective lens 40 is compensated, the pumping light is collected on a center of the spot pattern of the erasing light in the donut shape without causing displacement from the axis, which easily satisfies conditions to present the ultra-high resolution function. Therefore, although it is conventionally believed that it is inevitable to have the modulation optical element requiring highly precise processing technology and adjustment technology, it is possible, according to the present embodiment, to manufacture the modulation optical element 38 with a flexible optical designing and also to present the ultra-high resolution function with a simple optical adjustment.

The modulation optical element 38 is not limited to the annular shape as shown in FIG. 2 but may have phases gradually change about the optical axis as shown in FIG. 1. In addition, it is also possible to use a modulation optical element 50 as shown in FIG. 5(*a*) to (*c*).

Figure 5:
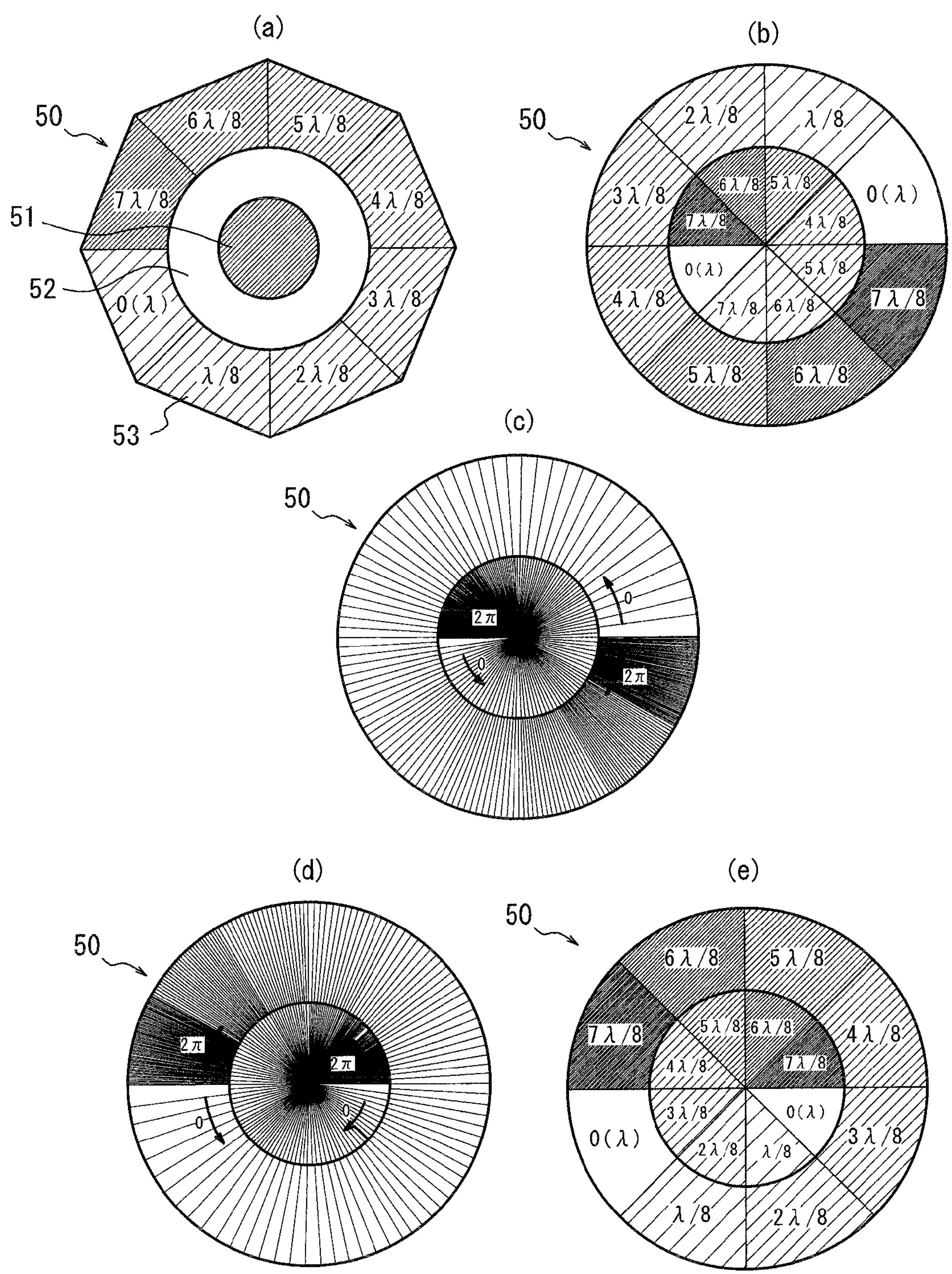
FIG. 5 shows other three examples of the modulation optical element usable for the super-high resolution microscope in FIG. 4.

The modulation optical element 50 shown in FIG. 5(*a*) is of a hybrid type combining the modulation optical element 1 shown in FIG. 1 and the modulation optical element 10 shown in FIG. 2 and has a center region 51, an intermediate region 52 and a periphery region 53 all in the annular shape. The center region 51 and the intermediate region 52 are formed in the similar manner as the center region 11 and the periphery region 12 of the modulation optical element 10 shown in FIG. 2. In a similar manner as the modulation optical element 1 shown in FIG. 1, the periphery region 53 is formed to have the plurality of optical multilayer regions radially divided (into 8 regions in FIG. 5(*a*)) such that the phase difference revolves by $2\pi$ for the erasing light.

In addition, it is preferred that the modulation optical element 50 is formed such that the polarization of the erasing light transmitting through each of the regions is different from one another, in order to avoid interference between the erasing light transmitting through the center region 51 and the intermediate region 52 and the erasing light transmitting through the periphery region 53. For example, the center region 51 and the intermediate region 52 are formed such that the erasing light transmitting therethrough has a clockwise circular polarization, whereas the periphery region 53 is formed such that the erasing light transmitting therethrough has a counterclockwise circular polarization.

Figure 6:
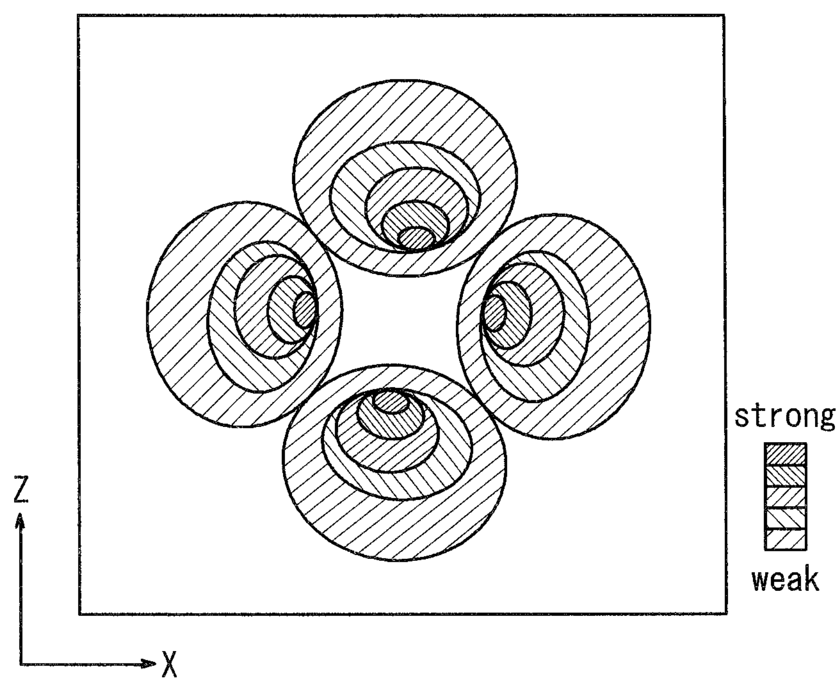
FIG. 6 is a diagram illustrating an intensity distribution of beams formed at a focal point and at back and forward thereof in using the modulation optical element in FIG. 5.

By collecting the erasing light having transmitted through the modulation optical element 50 with the microscope objective lens 40, it is possible to form a beam shape with an intensity distribution having an isotropic three dimensional dark hole as shown in FIG. 6 on the focal point and around it. In FIG. 6, z and x represent a direction of the optical axis and a direction orthogonal to the optical axis, respectively. Accordingly, a combination with the confocal optical system enables to obtain a resolution function in a direction of a depth of the sample 42.

Each of the modulation optical element 50 shown in FIG. 5(*b*) and that in FIG. 5(*c*) has a double ring structure. In FIGS. 5(*b*) and (*c*), an inner annular region and an outer annular region change the phase distribution of the erasing light by $2\pi$ about the optical axis, while having a rotary direction of a phase shift in an opposite direction to one another relative to the optical axis. FIG. 5(*b*) shows an exemplary configuration of quantization of a phase shift quantity by radially dividing each of the inner annular region and the outer annular region into 8 regions. FIG. 5(*c*) shows an exemplary configuration gradually changing the phase shift quantity of each of the inner annular region and the outer annular region about the optical axis.

In using the modulation optical element 50 shown in FIGS. 5(*b*) and (*c*), the electric field is compensated by adding an amplitude intensity of the erasing light having passed therethrough in a radial direction. Accordingly, with a function equal to that of the modulation optical element 10 of a dark hole type shown in FIG. 2, it is possible to generate an interference region for receiving no ultra-fine light not only at a focal point but also on the optical plane by collecting the erasing light, having passed through the modulation optical element 50, with the microscope objective lens. Each of the annular regions is preferably configured such that the phase continuously and smoothly changes as shown in FIG. 5(*c*). However, if each of the annular regions is coated with an optical thin film, it is easier, in consideration of an actual manufacturing process, to manufacture by quantization in eight phases as shown in FIG. 5(*b*). In addition, by using the optical multilayer as a means for providing a phase modulation in the similar manner as the modulation optical element 10 shown in FIG. 2, it is possible to shape a beam having the dark hole by phase modulation of only the erasing light, without phase modulation of the pumping light.

In the same manner, the modulation optical element 50 shown in such as FIG. 5(*d*) or (*e*) can be also applied to a surer-resolution microscope. The phase turning direction of FIGS. 5(*d*) and (*e*) is opposite to that of FIGS. 5(*c*) and (*b*). Using the phase modulation patterns of FIGS. 5(*d*) and (*e*), a focused erase beam with the three-dimensional doughnut hole shown in FIG. 6 can be generated, because electric fields in the outer and inner zone are cancelled and create a zero intensity hole at the focal point.

Second Embodiment

Figure 7:
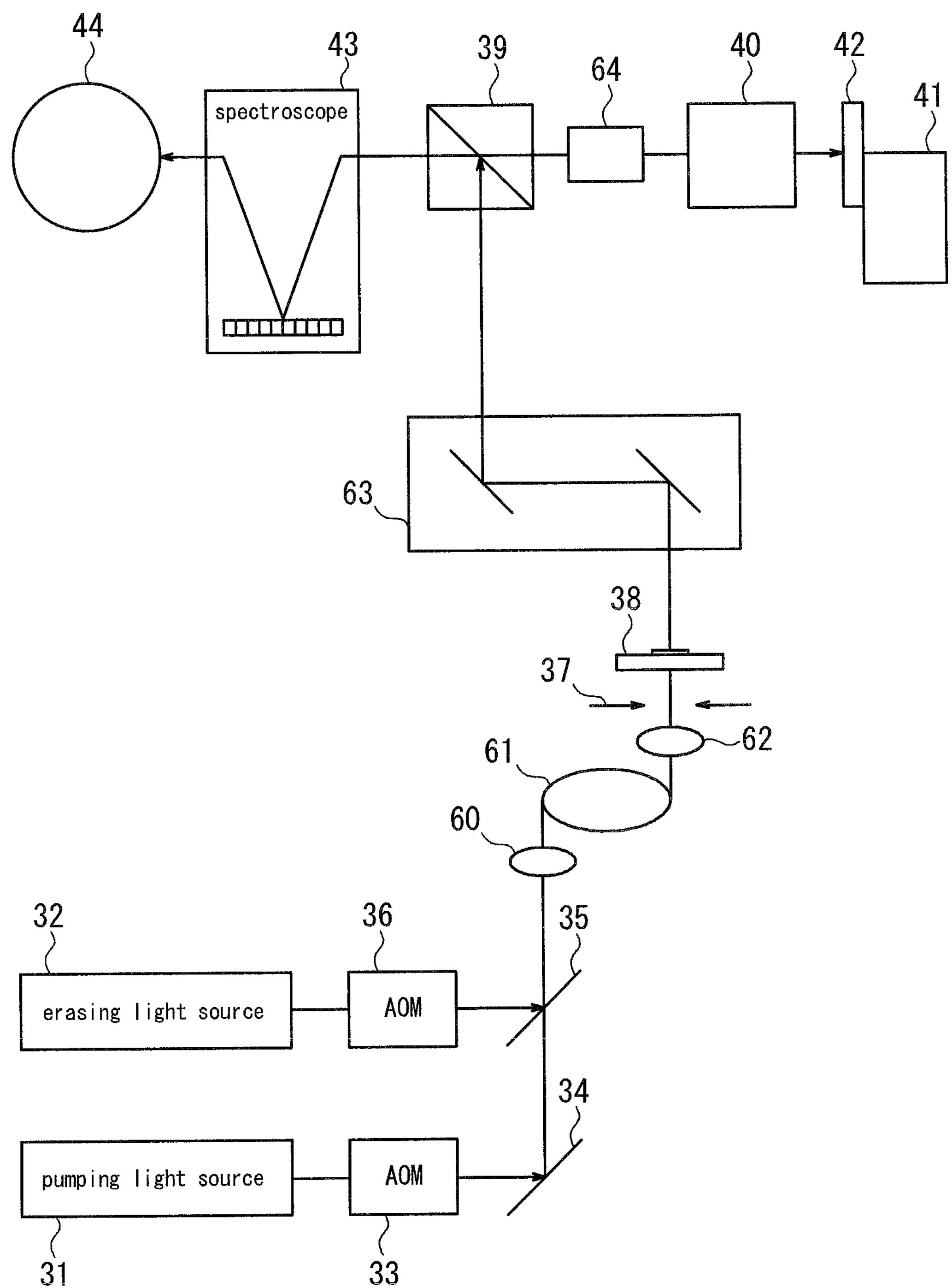
FIG. 7 is a diagram illustrating a schematic constitution of a main section of a super-high resolution microscope according to a second embodiment.

FIG. 7 is a diagram illustrating a schematic configuration of a main section of an ultra-high resolution microscope according to a second embodiment of the present invention. It is to be noted that components in FIG. 7 having the same functions as those shown in FIG. 4 are provided with the same reference signs and descriptions thereof are omitted. In the ultra-high resolution microscope, similar to that shown in FIG. 4, the pumping light and the erasing light coaxially combined by the dichroic mirror 35 is collected by a collective lens 60 and enters a single mode fiber 61. The pumping light and the erasing light exiting the single mode fiber 61 are converted into parallel lights by a collimator lens 62 and are incident on the modulation optical element 38 via the iris 37.

In addition, the pumping light and the erasing light having passed through the modulation optical element 38 is incident on the beam splitter 39 via a galvano scanner unit 63 and, after being reflected by the beam splitter 39, collected on the sample 42 held on the sample stage 41 by the microscope objective lens 40 via a pupil projection lens 64. Thereby, the sample 42 is scanned in two dimensions with the pumping light and the erasing light. The light obtained from the sample 42, after collected by the microscope objective lens 40, transmits through the pupil projection lens 64 and the beam splitter 39 and is dispersed by the spectroscope 43, such that the signal light (fluorescence) of a necessary wavelength component is received by the photodetector 44 and, based on its output, a fluorescence image of the sample 42 is generated.

According to the ultra-high resolution microscope of the present embodiment, in a similar manner to the microscope of the first embodiment, it is possible to find a condition to satisfy the formula (2) by a simple operation to adjust the diameters of the luminous flux of the pumping light and the erasing light and, as necessary, the optical axis (eccentricity) by the iris 37. That is, for the erasing light, it is possible to fully adjust a ratio of the dimensions of the center region having the optical multilayer and the transmittance dimensions of the peripheral region of the modulation optical element 38. Thereby, it is possible to present the ultra-high resolution function by easily compensating the manufacturing errors of the modulation optical element 38. Accordingly, it is possible to easily manufacture the modulation optical element 38 with a flexible optical designing.

In addition, since the pumping light and the erasing light are guided into the single mode fiber 61, which is commonly used, and extracted as the parallel lights by the collimate lens 62, it is possible to make the pumping light and the erasing light of complete spherical waves into the modulation optical element 38. Accordingly, it is possible to form a more accurate spot pattern of the erasing light in the donut shape on the focal plane of the sample 42.

Moreover, since the pumping light and the erasing light are scanned in two dimensions by the galvano scanner unit 63, it can improve accuracy in measurement and shorten a measurement time, in comparison to the microscope which scans the sample 42 in two dimensions by moving the sample stage 41 as shown in FIG. 4. Furthermore, since the pumping light and the erasing light scanned in two dimensions by the galvano scanner unit 63 are collected on the sample 42 by the microscope objective lens 40 via the pupil projection lens 64, the lights can be collected on the focal plane without causing aberration.

Third Embodiment

Figure 8:
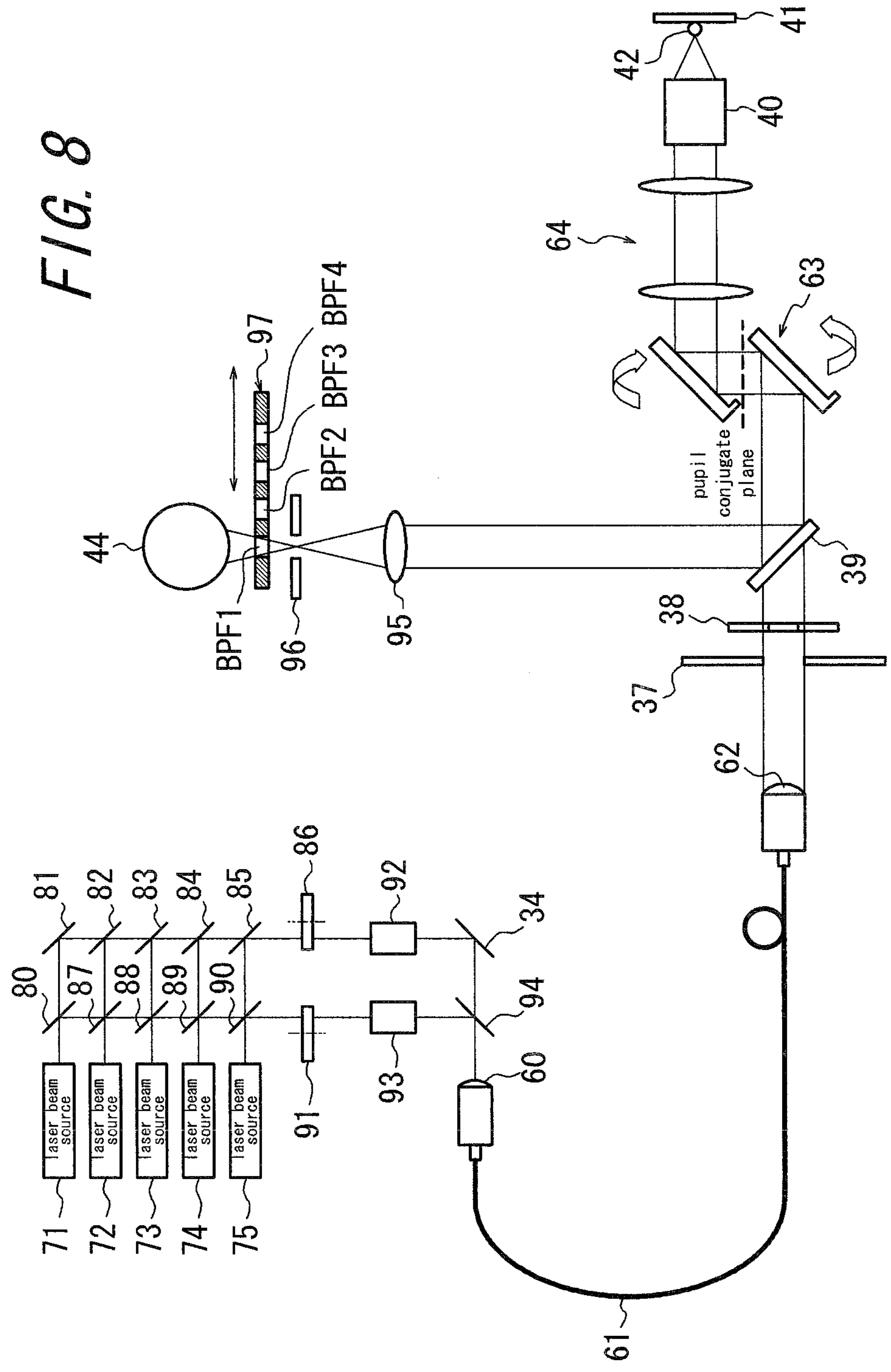
FIG. 8 is a diagram illustrating a schematic configuration of a main section of a super-high resolution microscope according to a third embodiment.

FIG. 8 is a diagram illustrating a schematic configuration of a main section of an ultra-high resolution microscope according to a third embodiment of the present invention. It is to be noted that components in FIG. 8 having the same functions as those shown in FIG. 7 are provided with the same reference signs and descriptions thereof are omitted. The ultra-high resolution microscope according to the present embodiment is configured to be able to handle a variety of dye molecules. That is, particularly in biological discipline, various observation subjects are stained with a variety of dyes for explanations of life phenomena.

Here, although fluorescence suppression is observed in numerous molecules, an excitation wavelength and a fluorescence wavelength widely differ among the molecules. Generally, although a fluorescence suppression effect can be induced by illuminating the erasing light of a longer wavelength than the fluorescence wavelength band in which the molecule is not excited to the first excited state (S1 state), its presentation level depends on the wavelength of the erasing light. In addition, in order to excite the molecule to the S1 state with less illumination intensity, it is necessary to optimize the wavelength of the pumping light.

In particular, it is desired to have a flexible microscope system capable of selecting the pumping light wavelength and the erasing light wavelength that can efficiently induce the fluorescence suppression effect based on the dye to use and detecting fluorescence with high sensitivity without mixing the pumping light and the erasing light into the detector. More particularly, there is a need for a versatile microscope capable of dealing with a variety of fluorescence dye that emits light between an ultraviolet region and a near-infrared region.

The ultra-high resolution microscope according to the present embodiment meets the above need and has three or more laser beam sources with different emission wavelengths. FIG. 8 illustrates an example having five laser beam sources 71-75 with different emission wavelengths. The laser beam source 71 emits light of an emission wavelength λ1 of 405 nm, for example, and may excite dye such as fluorescence protein CFP (Cyan Fluorescence Protein) and the like. The laser beam source 72 emits light of an emission wavelength λ2 of 480 nm, for example, and may excite typical common dyes, such as Alexa 488, FITC (Fluorescein isothiocianate) and the like. The laser beam source 73 emits light of an emission wavelength λ3 of 532 nm, for example, and may excite dyes, such as Alexa 532, Nile Red and the like. The laser beam source 74 emits light of an emission wavelength λ4 of 639 nm, for example, and may excite dyes, such as Texas Red and the like. The laser beam source 75 emits light of an emission wavelength λ5 of 730 nm, for example, and may excite dyes corresponding to a near infrared light, such as Cy7 of canine system and the like.

The laser beam sources 72-75, other than the laser beam source 71, are used also as the erasing light sources. That is, the fluorescence suppression effect can be induced by the erasing light of a longer wavelength which does not excite the dye to emit fluorescence as stated above. Accordingly, if the laser beam source 71 is used as the pumping light source, for example, any of the laser beam sources 72-75 may be used as the erasing light source in accordance with fluorescence dye to use. In addition, in using the laser beam source 73 as the pumping light source, the laser beam source 74 or the laser beam source 75 may be used as the erasing light source.

According to analyses by the present inventor, a relation between a fluorescence band of the dye and the wavelength of the pumping light and that of the erasing light is as follows. That is, the fluorescence band is positioned in an intermediate wavelength band of the pumping light and the erasing light. Accordingly, it is possible to detect fluorescence by separating it from scattering ray of the pumping light and the erasing light, by providing one or more optical filters immediately before the photodetector, in particular, by installing a band pass filter having a transmittance in the intermediate wavelength band of the pumping light and the erasing light or by installing two notch filters for blocking the wavelength of the pumping light and that of the erasing light.

The ultra-high resolution microscope according to the present embodiment has the laser beam sources 71-75 capable of oscillating at five different wavelengths 405 nm (λ1), 480 nm (λ2), 532 nm (λ3), 639 nm (λ4) and 730 nm (λ5), respectively, as stated above. In principle, it is thus possible to perform ultra-high resolution measurement with ten wavelength pairs of 405 nm-480 nm, 405 nm-532 nm, 405 nm-639 nm, 405 nm-730 nm, 480 nm-532 nm, 480 nm-639 nm, 480 nm-730 nm, 532 nm-639 nm, 532 nm-730 nm, and 639 nm-730 nm.

Figure 9:
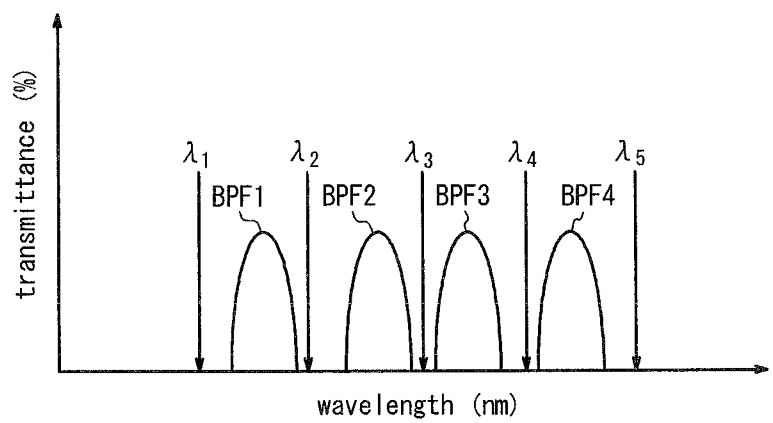
FIG. 9 is a diagram illustrating an exemplary bandpass filter usable in the third embodiment.

However, if the pumping light and the erasing light of the ultra-high resolution microscope form an image while being out of alignment with each other in the optical axis direction, in other words, if there is the chromatic aberration on the axis, a dramatic improvement in the resolution cannot be expected generally. Accordingly, it is preferred to measure the image with a combination of lights of adjacent wavelengths that hardly causes the chromatic aberration. In this case, it is preferred to prepare, as filters used for fluorescence detection, bandpass filters BPF1 to BPF4 having the transmittance between adjacent emission wavelengths λ1-λ2, λ2-λ3, λ3-λ4 and λ4-λ5 as shown in FIG. 9 and to switch them appropriately in accordance with the combination of the light sources.

Figure 10:
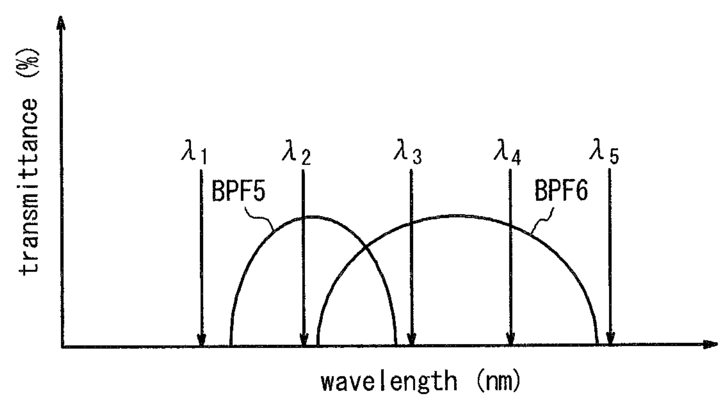
FIG. 10 is a diagram illustrating another exemplary bandpass filter usable in the third embodiment.

It is to be noted that, if the chromatic aberration of the optical system of the microscope can be ignored, it allows for a combination of distant emission wavelengths such as, for example, a combination of the oscillation wavelengths λ1 and λ3 or a combination of the emission wavelengths λ2 and λ5. In this case, bandpass filters BPF5, BPF6 having the transmittance between adjacent emission wavelengths λ1-λ3 and λ2-λ5 as shown in FIG. 10 are prepared and switched appropriately in accordance with a combination of the light sources. Moreover, if there is no auxiliary light generated from the sample caused by emission of the erasing light or the pumping light, it is possible to insert a plurality of notch filters capable of blocking only the emission wavelength of the light source into the optical path of a detection optical system.

As shown in FIG. 8, the laser beam emitted from the laser beam source 71 is dispersed into two luminous flux by a beam splitter 80. Then, one of the luminous flux transmitting through the beam splitter 80, after reflected by a reflector 81, sequentially transmits through beam combiners 82, 83, 84 and 85 and is then incident on a rotary ND filter 86, whereas the other one of the luminous flux reflected by the beam splitter 80 sequentially transmits through beam splitters 87, 88, 89 and 90 and is then incident on a rotary ND filter 91.

The laser beam emitted from the laser beam source 72 is dispersed into two luminous flux by the beam splitter 87. Then, one of the luminous flux transmitting through the beam splitter 87, after reflected by the beam combiner 82 and coaxially combined with the optical path of the laser beam from the reflector 81, sequentially transmits through the beam combiners 83, 84 and 85 and is incident on the rotary ND filter 86. The other one of the luminous flux reflected by the beam splitter 87, after coaxially combined with the optical path of the laser beam from the beam splitter 80, sequentially transmits through the beam splitters 88, 89 and 90 and is incident on the rotary ND filter 91.

The laser beam emitted from the laser beam source 73 is dispersed into two luminous flux by the beam splitter 88. Then, one of the luminous flux transmitting through the beam splitter 88, after reflected by the beam combiner 83 and coaxially combined with the optical path of the laser beam from the beam combiner 82, sequentially transmits through the beam combiners 84, 85 and is incident on the rotary ND filter 86. The other one of the luminous flux reflected by the beam splitter 88, after coaxially combined with the optical path of the laser beam from the beam splitter 87, sequentially transmits through the beam splitters 89, 90 and is incident on the rotary ND filter 91.

The laser beam emitted from the laser beam source 74 is dispersed into two luminous flux by the beam splitter 89. Then, one of the luminous flux transmitting through the beam splitter 89, after reflected by the beam combiner 84 and coaxially combined with the optical path of the laser beam from the beam combiner 83, transmits through the beam combiner 85 and is incident on the rotary ND filter 86. The other one of the luminous flux reflected by the beam splitter 89, after coaxially combined with the optical path of the laser beam from the beam splitter 88, transmits through the beam splitter 90 and is incident on the rotary ND filter 91.

The laser beam emitted from the laser beam source 75 is dispersed into two luminous flux by the beam splitter 90. Then, one of the luminous flux transmitting through the beam splitter 90, after reflected by the beam combiner 85 and coaxially combined with the optical path of the laser beam from the beam combiner 84, is incident on the rotary ND filter 86. The other one of the luminous flux reflected by the beam splitter 90, after coaxially combined with the optical path of the laser beam from the beam splitter 89, is incident on the rotary ND filter 91.

Each of the rotary ND filters 86, 91 is configured to have a plurality of ND filters with different transmittances disposed on the same circumference and to dispose the ND filters with desired transmittances on a corresponding optical axis, in order to obtain a transmitted light with a desired intensity. The light having transmitted through the rotary ND filter 86 is incident on an acousto-optical wavelength-tunable filter 92, whereas the light having transmitted through the rotary ND filter 91 is incident on an acousto-optical wavelength-tunable filter 93.

The acousto-optical wavelength-tunable filters 92, 93 select light of a desired wavelength by controlling a frequency of a surface acoustic wave excited. Thereby, pseudo-pulsed pumping light of the desired wavelength is obtained from the acousto-optical wavelength-tunable filter 92, whereas pseudo-pulsed erasing light of the desired wavelength is obtained from the acousto-optical wavelength-tunable filter 93.

The pumping light obtained from the acousto-optical wavelength-tunable filter 92 is reflected by the reflector 34, transmits through a beam combiner 94 and then enters the single mode fiber 61 via the collective lens 60. Meanwhile, the erasing light obtained from the acousto-optical wavelength-tunable filter 93 is reflected by the beam combiner 94 and coaxially combined with the optical axis of the pumping light and then enters the single mode fiber 61 via the collective lens 60.

That is, the ultra-high resolution microscope according to the present embodiment selects and drives two laser beam sources, among the laser beam sources 71-75, having adjacent emission wavelengths corresponding to the desired wavelengths of the pumping light and the erasing light. Next, the laser beam emitted from these two laser beam sources transmits through the rotary ND filter 86 and the acousto-optical wavelength-tunable filter 92, as well as the rotary ND filter 91 and the acousto-optical wavelength-tunable filter 93. Thereby, the pumping light and the erasing light, that are pseudo-pulsed so as to effectively present the fluorescence suppression effect, are obtained from the acousto-optical wavelength-tunable filters 92, 93. Then, the pumping light and the erasing light are coaxially combined by the beam combiner 94 and enter the single mode fiber 61 via the collective lens 60.

The pumping light and the erasing light exited from the single mode fiber 61, after converted into the parallel lights by the collimator lens 62, is incident on the modulation optical element 38 via the iris 37. Then, the pumping light and the erasing light having transmitted through the modulation optical element 38, after having transmitted through the beam splitter 39, are collected on the sample 42, held on the sample stage 41, by the microscope objective lens 40 via the galvano scanner unit 63 and the pupil projection lens 64. Thereby, the sample 42 is scanned in two dimensions by the pumping light and the erasing light.

in addition, the light obtained from the sample 42, after collected by the microscope objective lens 40, is reflected by the beam splitter 39 after transmitting through the pupil projection lens 64 and the galvano scanner unit 63. The light from the sample 42 reflected by the beam splitter 39 travels through the collective lens 95, a confocal pinhole 96 and a filter unit 97 and the signal light (fluorescence) of necessary wavelength component is received by the photodetector 44. Based on output of the photodetector 44, the fluorescence image of the sample 42 is generated.

Here, as shown in FIG. 9, the filter unit 97 holds four independent bandpass filters BPF1-BPF4 having the transmittance between the adjacent emission wavelengths of five different laser beam sources 71-75 in a linear arrangement and disposed slidably relative to the optical path of the photodetector 44. Then, a desired bandpass filter, that is, the bandpass filter having the transmittance between the emission wavelengths of two selected laser beam sources is inserted into the optical path of the photodetector 44. It is also possible to configure the filter unit 97 such that the rotary filter holds the bandpass filters BPF1-BPF4 and the desired bandpass filter is inserted into the optical path of the photodetector as being rotated.

According to the ultra-high resolution microscope of the present embodiment, it is possible to obtain the same effect as that of the second embodiment. In addition, this microscope has a plurality of laser beam sources 71-75 with different emission wavelengths and a plurality of bandpass filters BPF1-BPF4 having the transmittance between the adjacent emission wavelengths. Accordingly, it allows for an easy selection of the wavelengths of the pumping light and the erasing light capable of effectively inducing the fluorescence suppression effect in accordance with the dye used and accomplishment of a flexible microscopic system capable of detecting fluorescence from the sample 42 with high sensitivity by preventing interfusion of the pumping light and the erasing light into the photodetector 44. Moreover, with the confocal pinhole 96 disposed on an incidence side of the photodetector 44, it is possible to improve S/N by further cutting scattering light and the like, as well as to obtain a spatial resolution to the direction of the depth of the sample 42.

In the configuration shown in FIG. 8, if the dye molecule has a large stoke shift such as fluorescence protein, that is, if the dye molecule has a fluorescence wavelength significantly shifts to a long wavelength side relative to an absorption wavelength of the pumping light, it is possible to combine the laser beam sources with distance emission wavelengths, such as the laser beam source 71 and the laser beam source 73. In this case, it is configured such that, in accordance with the combination of the emission wavelengths, the BPF having a transmittance property as shown in FIG. 10 is held by the filter unit 97 such that the corresponding BPF is inserted into the incident optical path of the photodetector 44.

In addition, in the configuration shown in FIG. 8, it is also possible to dispose the spectroscope on the incident optical path of the photodetector 44 between the beam splitter 39 and the collective lens 95 in the same manner as the embodiments shown in FIG. 4 and FIG. 7, such that the spectroscope disperses the signal light (fluorescence) of the desired wavelength to be received by the photodetector 44 via the collective lens 95, the confocal pinhole 96 and the filter unit 97. Thereby, it is possible to improve SN of the signal light and to detect the signal light with high sensitivity.

Figure 11:
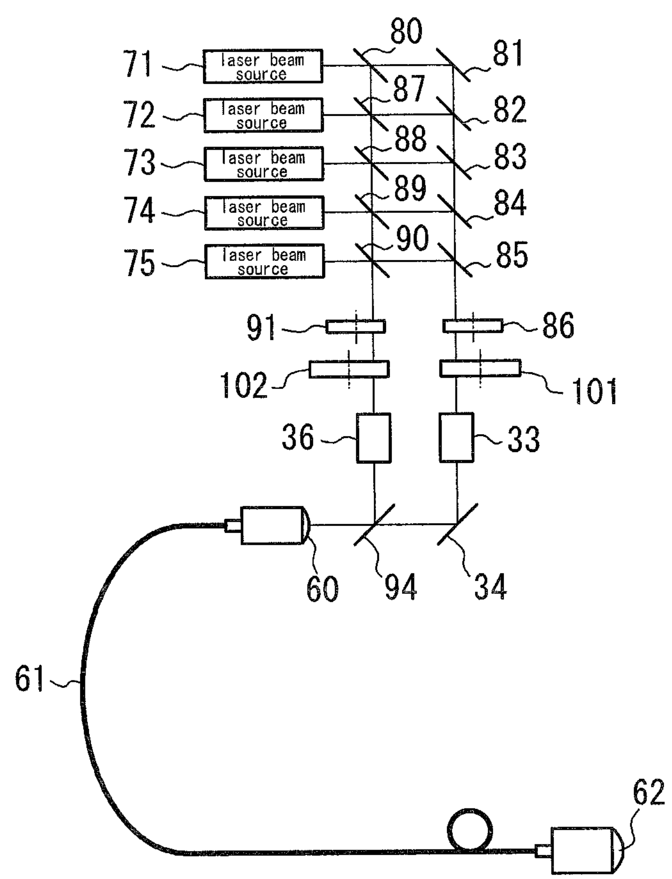
FIG. 11 is a partial configuration diagram illustrating an exemplary variant of the third embodiment.
Figure 12:
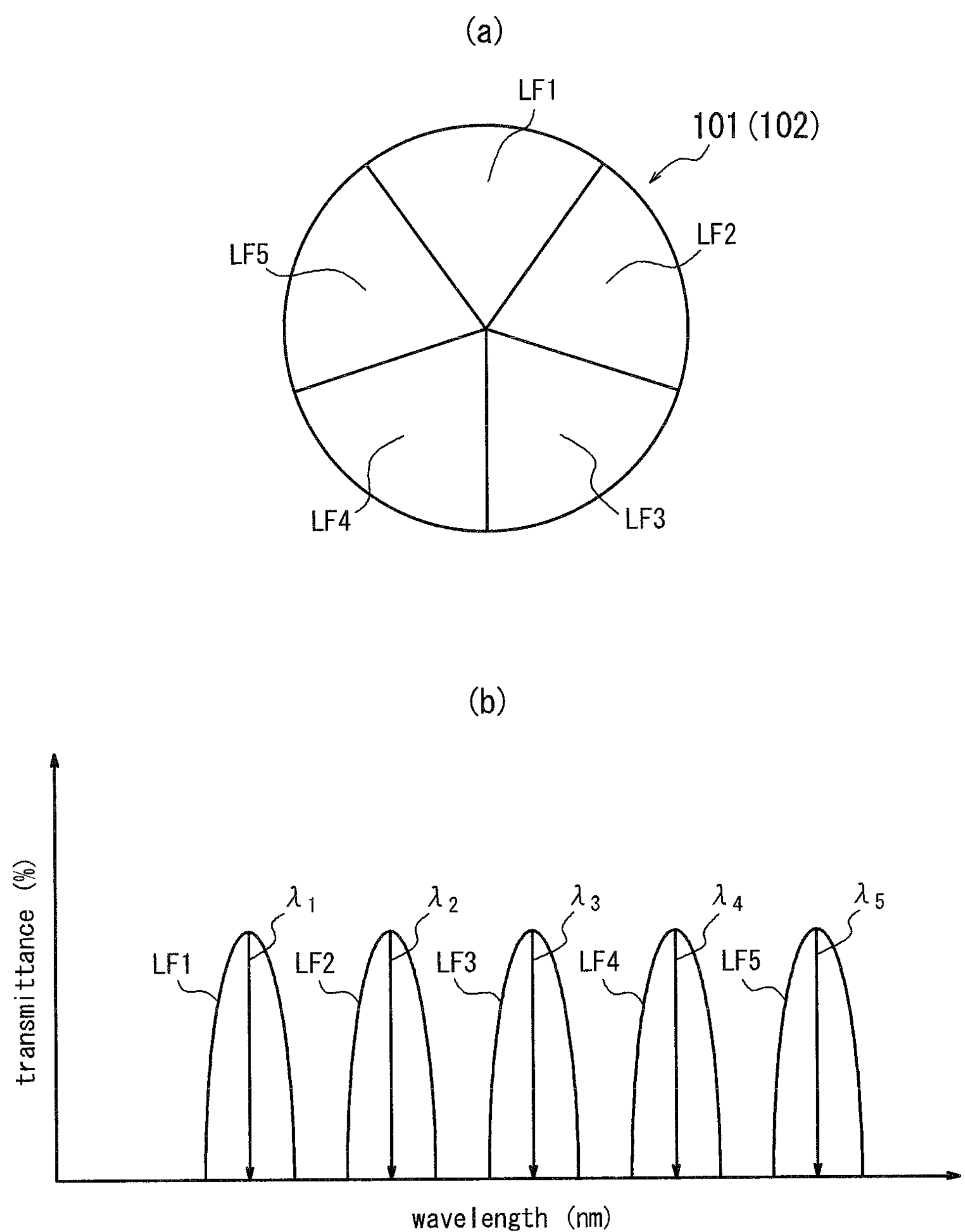
FIG. 12 is a diagram illustrating a rotary filter shown in FIG. 11.

Moreover, it is also possible, as shown by a partial configuration diagram in FIG. 11, to obtain the pumping light and erasing light, each of which are pseudo-pulsed so as to effectively present the fluorescence suppression effect, by providing rotary filters 101, 102 and AOMs 33, 36 in place of the acousto-optical wavelength-tunable filters 92, 93 in FIG. 8. Here, as shown in FIG. 12(*a*), each of the rotary filters 101, 102 is configured to hold laser line filters LF1-LF5 respectively corresponding to each of the laser beam sources 71-75 and to be inserted as rotated such that a desired line filter corresponding to the selected laser beam source is inserted into the optical path. As shown in FIG. 12(*b*), the laser line filters LF1-LF5 have the transmittance property of a narrow band to allow the lights of the predetermined emission wavelengths λ1, λ2, λ3, λ4 and λ5 of the laser beam sources 71-75 to effectively transmit therethrough.

Then, the laser beam of the desired wavelength is obtained by the rotary filter 101 from the two-color laser beam having transmitted through the rotary ND filter 86, and the intensity of the laser beam is modulated by the AOM 33 in order to obtain a pseudo-pulsed desired pumping light. Similarly, the laser beam of the desired wavelength is obtained by the rotary filter 102 from the two-color laser beam having transmitted through the rotary ND filter 91, and the intensity of the laser beam is modulated by the AOM 36 in order to obtain a pseudo-pulsed desired erasing light. Other configurations are the same as those in FIG. 8.

Fourth Embodiment

Figure 13:
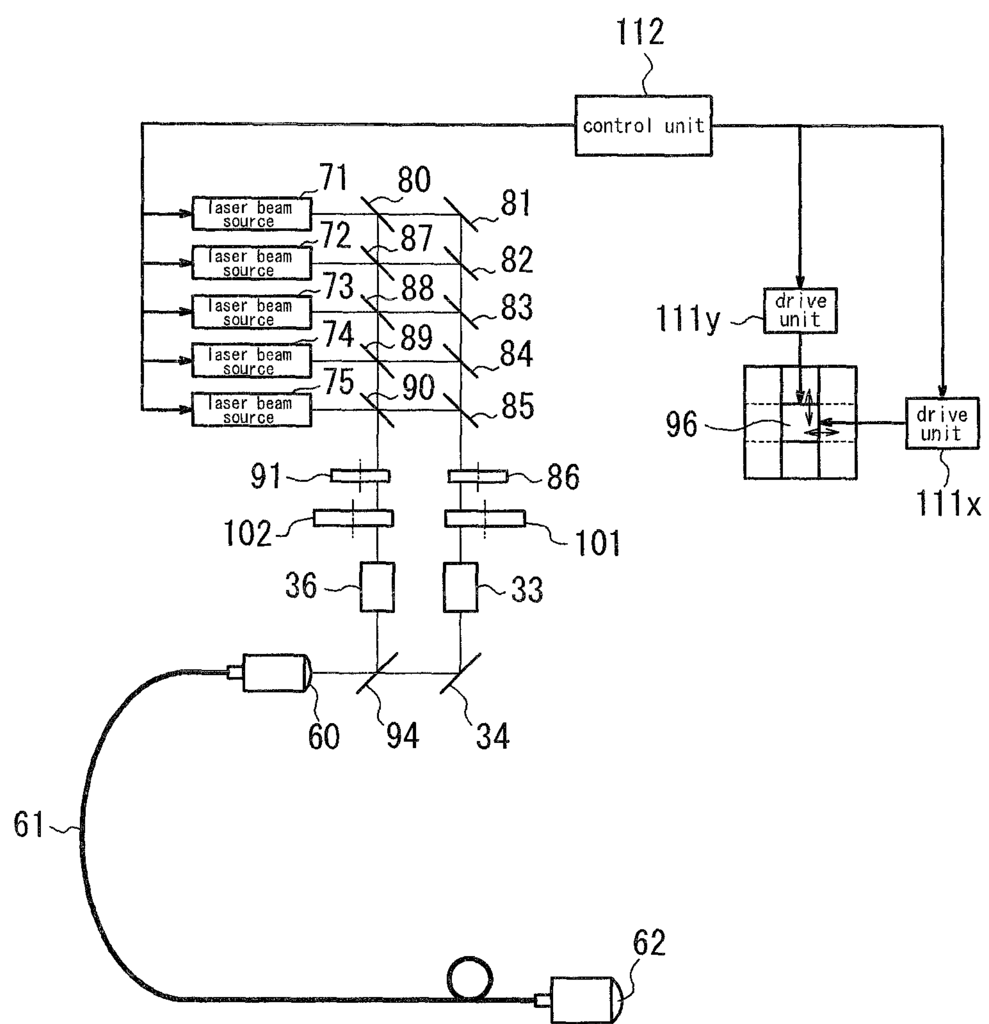
FIG. 13 is a diagram illustrating a schematic configuration of a main section of a super-high resolution microscope according to a fourth embodiment.

FIG. 13 is a diagram illustrating a schematic configuration of a main section of an ultra-high resolution microscope according to a fourth embodiment of the present invention. The microscope according to the present embodiment has a configuration shown in FIG. 11 in which the confocal pinhole 96 for the photodetector 44 shown in FIG. 8 is formed into a rectangular aperture with changeable slit widths in an X direction and a Y direction, as shown in FIG. 13, each of which can be adjusted by corresponding drive units 111*x*, 111*y* constructed of PZT or the like. In addition, the microscope according to the present embodiment has a control unit 112 for the laser beam sources 71-75 and the drive unit 111*x*, 111*y*. Thereby, drive and a combination of the laser beam sources 71-75, that is, generation of the pumping light and the erasing light to be used is controlled and, via the drive units 111*x*, 111*y*, an aperture a (in this case, a diameter of an inscribed circle) of the confocal point pinhole 96 is controlled to satisfy the following formula (4) based on the pumping light and the erasing light to be generated.

[Formula 4]

$$0.61\frac{\lambda_p}{NA}M > a \geq 0.49\sqrt{\frac{\varepsilon_e}{\tau\sigma_{dip}C_{e0}}}\frac{\lambda_e}{NA}M \tag{4}$$

NA: numerical aperture of objective lens

M: magnification of photodetector for focusing image on object side

λp: pumping light wavelength

λe: erasing light wavelength $\sigma_{dip}$: fluorescent suppression cross-section dimensions $C_{e0}$: peak intensity of erasing light $\epsilon_e$: photon flux of erasing light That is, according to the present embodiment, the aperture a of the confocal pinhole 96 is controlled to be under a diffraction limit based on Rayleigh criterion and equal to or over a half width of a point spread function for the photodetector 44 (see FIG. 8). Other configurations are the same as those in FIG. 8 and FIG. 11. Therefore, components having the same functions as those shown in FIG. 8 and FIG. 11 are provided with the same reference signs and descriptions thereof are omitted.

Figure 14:
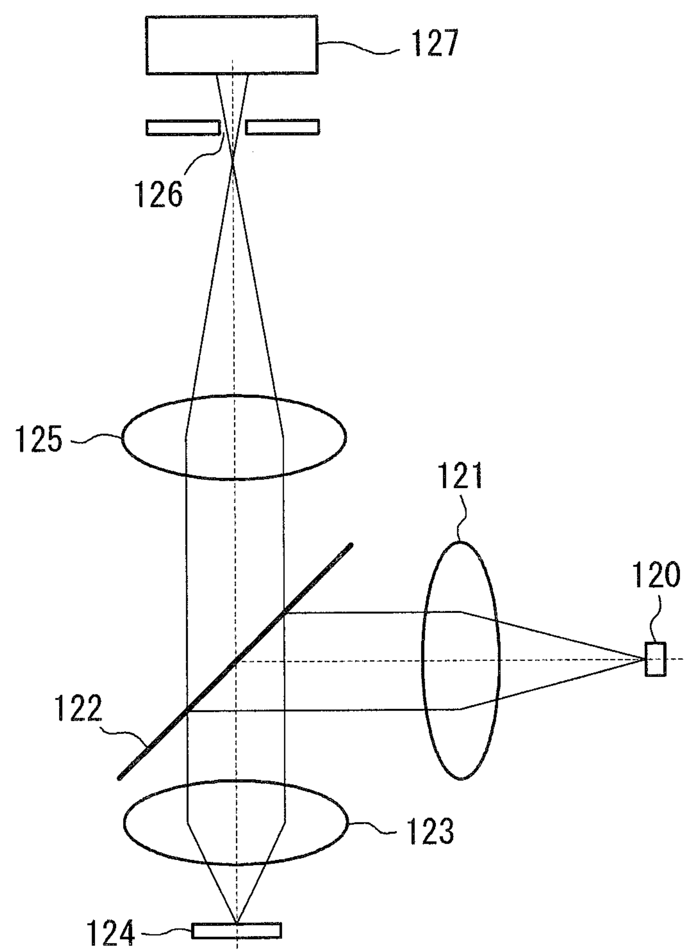
FIG. 14 is a pattern diagram illustrating a basic configuration of a confocal microscope.

Now, the point spread function (PSF; Point Spread Function) of the confocal microscope will be described. FIG. 14 is a pattern diagram illustrating a basic configuration of the confocal microscope. In FIG. 14, the light emitted from a point light source 120 is collimated by a lens 121 and reflected by a beam splitter 122 to be collected on an object 124 by an objective lens 123. In addition, the light (for example, fluorescence) from the object 124 is detected by a photodetector 127 after passing through the beam splitter 122, a collective lens 125 and a confocal pinhole 126.

In the confocal microscope shown in FIG. 14, the following formula (5) is satisfied, provided that $I_0(x, y)$ represents PSF for the substance by the objective lens 123, $I_d(x, y)$ represents PSF for the photodetector 127, d represents a coordinate of an aperture of the confocal pinhole 126, t represents the emission intensity distribution of the object 124, a magnification M of the objective lens 123 is 1, and h(x, y) represents PSF for the confocal microscope.

[Formula 5]

$$h(x,y)=\{I_0(I_d \otimes d)\} \otimes t \quad (5)$$

Note that $\otimes$ represents convolution.

Although it is defined as M=1 in the above formula for the sake of simplification, if M≠1, scaling is performed to the coordinates of the substance 124 and the photodetector 127. For example, provided that g(x,y) represents the image by the photodetector 127 and f(x, y) represents an original image of the substance 124, the following formula (6) is satisfied.

[Formula 6]

$$g(x) \otimes f(x)=\int g(x-t)f(t)dt \quad (6)$$

Here, if t is a delta function of t=δ(x,y), the above formula (5) becomes the following formula (7).

[Formula 7]

$$h(x,y)=I_0(I_d \otimes d) \quad (7)$$

Moreover, if d=δ(x,y), the above formula (7) becomes the following formula (8).

[Formula 8]

$$h(x,y)=I_0 I_d \quad (8)$$

As can be seen in the above formula (8), the resolution function of the confocal microscope is better than that of the microscope having no confocal pinhole. Here, for a normal confocal microscope, that is, the confocal microscope with no function to present the ultra-high resolution, both $I_0$ and $I_d$ are Gauss function. In contrast, for the ultra-high resolution microscope having the function to present the ultra-high resolution has a characteristic to have $I_0$ as Lorenz function and $I_d$ as Gaussian function. Accordingly, PSF differs depending on whether there is the confocal pinhole and the ultra-high resolution function.

Figure 15:
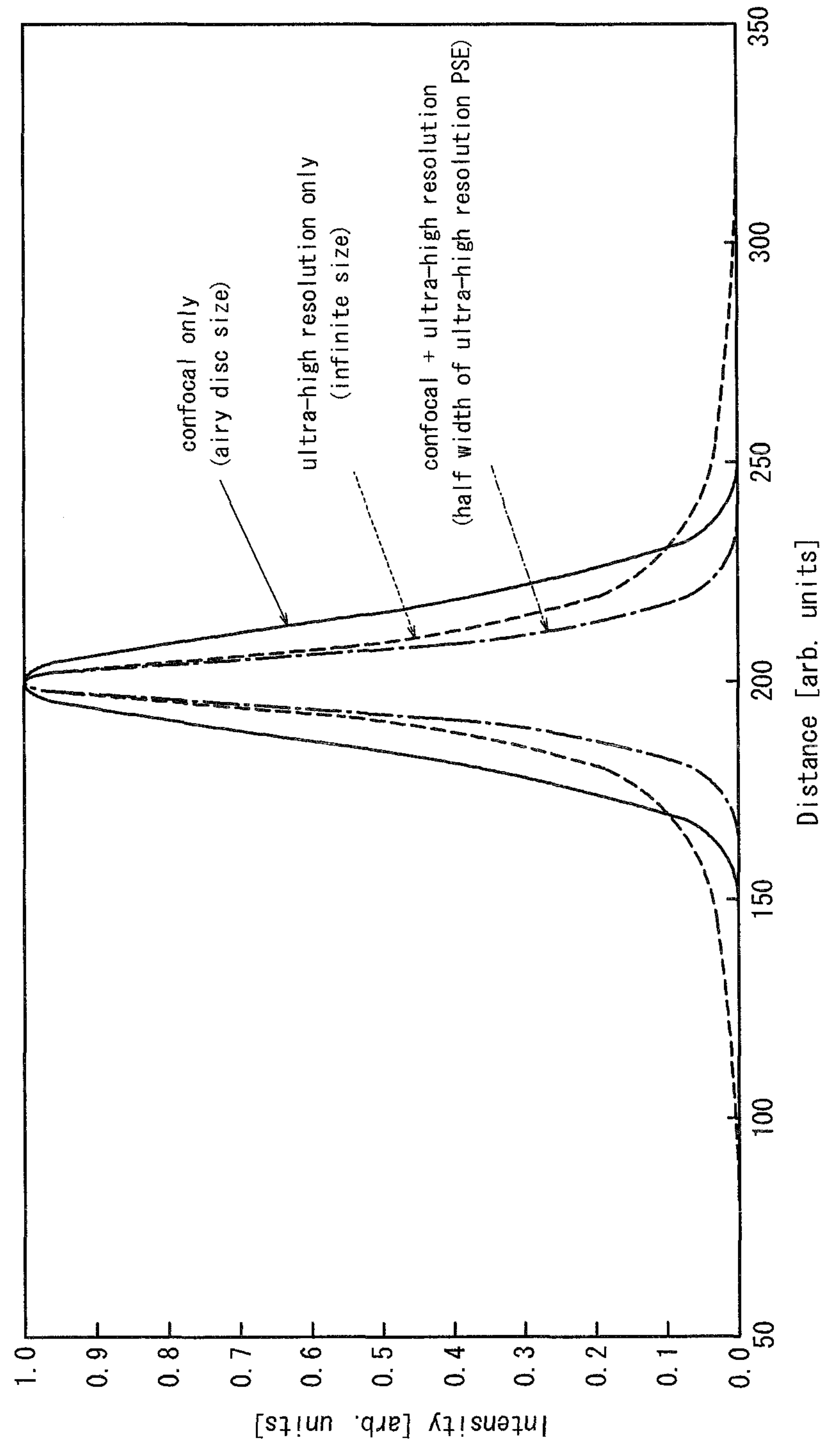
FIG. 15 is a diagram illustrating a comparison of a point image distribution function of each of the microscopes.

FIG. 15 is a diagram illustrating a comparison of PSF of each of the microscopes. In FIG. 15, a solid line indicates PSF of the normal confocal microscope having a confocal pinhole in an airy disc size. A broken line indicates PSF of an ultra-high resolution microscope having no confocal pinhole, that is, having an infinite size photodetector. A dashed line indicates PSF of an ultra-high resolution confocal microscope having the confocal pinhole with a diameter of a half width of the PSF.

Figure 16:
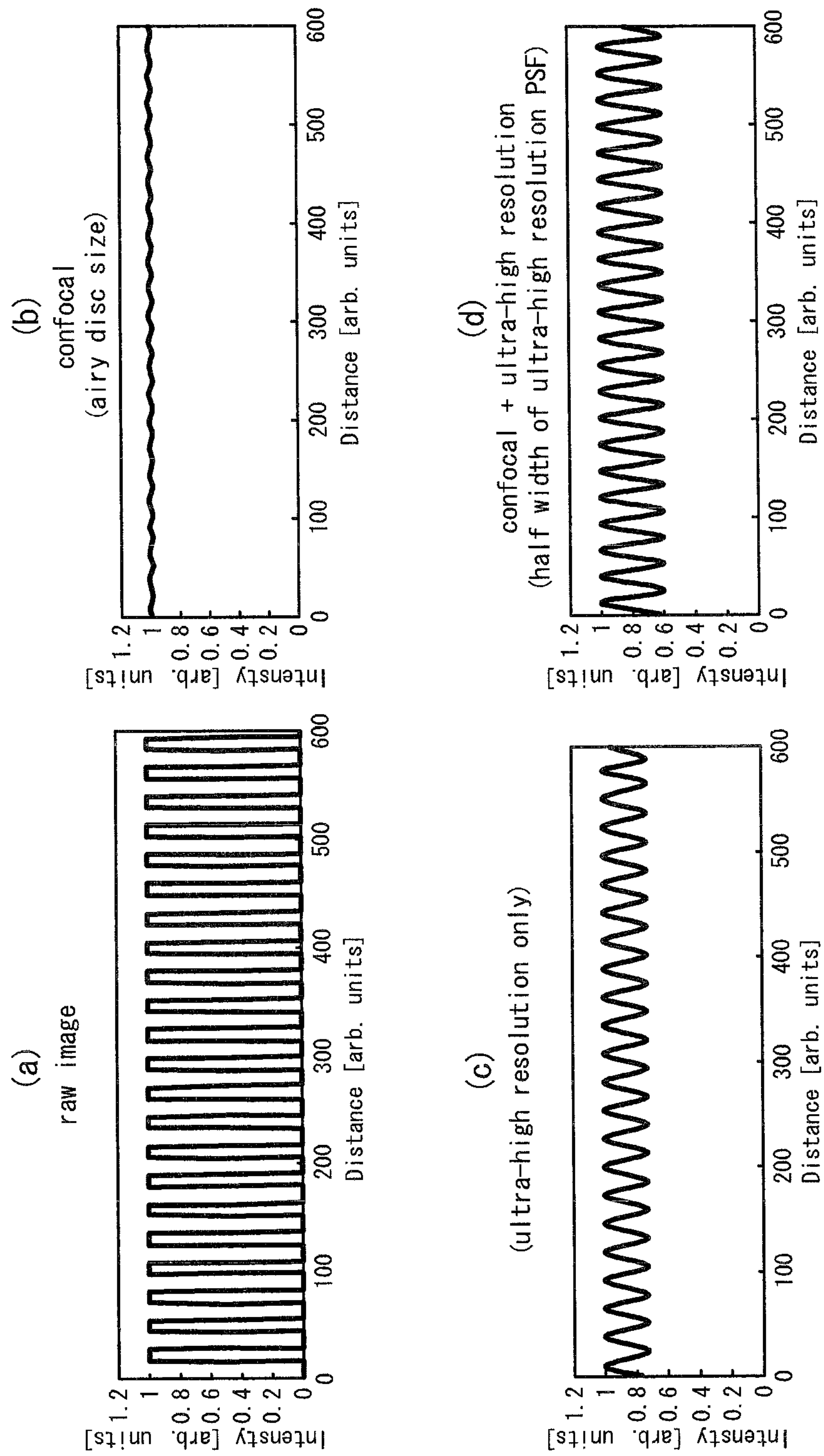
FIG. 16 is a diagram illustrating a contrast transfer function of a diffraction size limit of each of the microscopes.

FIG. 16(*a*) to (*d*) are diagrams illustrating contrast transfer function (CTF: Contrast Transfer Function) of the diffraction limit size of each of the microscopes. FIG. 16(*a*) shows a raw image of the diffraction limit size in a monochrome pattern. FIG. 16(*b*) shows CTF of the normal confocal microscope for the raw image in FIG. 16(*a*), FIG. 16(*c*) shows CTF of the ultra-high resolution microscope having no confocal pinhole for the raw image in FIG. 16(*a*), and FIG. 16(*d*) shows CTF of the ultra-high resolution confocal microscope for the raw image in FIG. 16(*a*).

As can be seen in FIG. 15, in comparison to PSF of the ultra-high resolution microscope having no confocal pinhole and PSF of the normal confocal microscope, PSF of the ultra-high resolution microscope having no confocal pinhole can reduce (narrow) the half width. As a result, as obvious from a comparison between in FIG. 16(*b*) and (*c*), the ultra-high resolution microscope, even having no confocal pinhole, can obtain CTF higher than that of the normal confocal microscope and a good contrast image.

As shown in FIG. 15, however, PSF of the ultra-high resolution microscope having no confocal pinhole spreads wider than PSF of the normal confocal microscope at a base portion of low intensity. Therefore, a good contrast image can be obtained with scattered samples such as fluorescence beads and thus the resolving power may be improved, whereas the contrast may be deteriorated with congested samples, as the components at the base portion overlap because of convolving of PSF of the object and PSF of the photodetector.

In contrast, as described in the present embodiment, the aperture of the confocal pinhole 96 is set half width, for example, of PSF of the photodetector 44 (see FIG. 8) in accordance with the pumping light and the erasing light to use, by the control unit 112. Thereby, as indicated by the dashed line in FIG. 15, it is possible to reduce spread of the base portion of low PSF intensity than PSF of the normal confocal microscope. As a result, as shown in FIG. 16(*d*), CTF is improved offering a sharp microscopic image. Especially in using congested samples as the observation object, it enables to obtain an ultra-high resolution microscopic image in high contrast.

That is, a size of the confocal pinhole of the normal confocal microscope is equal to or larger than that of the airy disc of the photodetector. This is not only because the spatial resolution is not improved by reducing the size smaller than the size of the airy disc but also because the detection signal is reduced and thus SN is deteriorated. However, according to the ultra-high resolution microscope of the present embodiment, with the small (narrow) half width of PSF of the photodetector 44, it is possible to further reduce the size of the confocal pinhole 96.

From results of simulations by the present inventor, it was confirmed that, it is possible, by reducing a diameter of the confocal pinhole 96 to the half width of PSF, to improve CTF significantly keeping reduction of photolepsy by the photodetector 44 at approximately only 30%. It is also confirmed that the modulation transfer function (MTF: Modulation Transfer Function) may also be improved. If the size of the confocal pinhole 96 is smaller than the half width of PSF of the photodetector 44, photolepsy of an optical signal component is reduced and thus SN is reduced unwantedly. Also, if a point image distribution function is sufficiently minute, the confocal pinhole itself is no longer necessary. Accordingly, it is preferred that the size of the confocal pinhole 96 satisfies the above formula (4).

It is to be understood that the present invention is not limited to the above embodiments but may be modified or varied in a multiple of manners. In the above embodiments, for example, the modulation optical element 38 may be disposed on the optical path of illumination and, simultaneously, on the optical path of a response light from the sample 42. In this case, the modulation optical element 38 is configured to have the transmittance to the response light (for example, fluorescence) from the sample 42. Such configuration is also applicable in using a single-color illumination light. In addition, in the configurations shown in FIG. 7 and FIG. 8, the modulation optical element 38 may be disposed on a pupil conjugate plane in the galvano scanner unit 63. Thereby, vignetting of luminous flux by scanning is not generated, which enables a stable formation of a desired spot pattern at all times.

In the above embodiments, in addition, the modulation optical element 38 may also be configured to have a plurality of optical multilayer regions radially divided about the optical axis revolving by 2π as shown in FIG. 1. In this case, it is possible to adjust the manufacturing errors of the modulation optical element 38 by an individual or integrated adjustment element.

Figure 17:
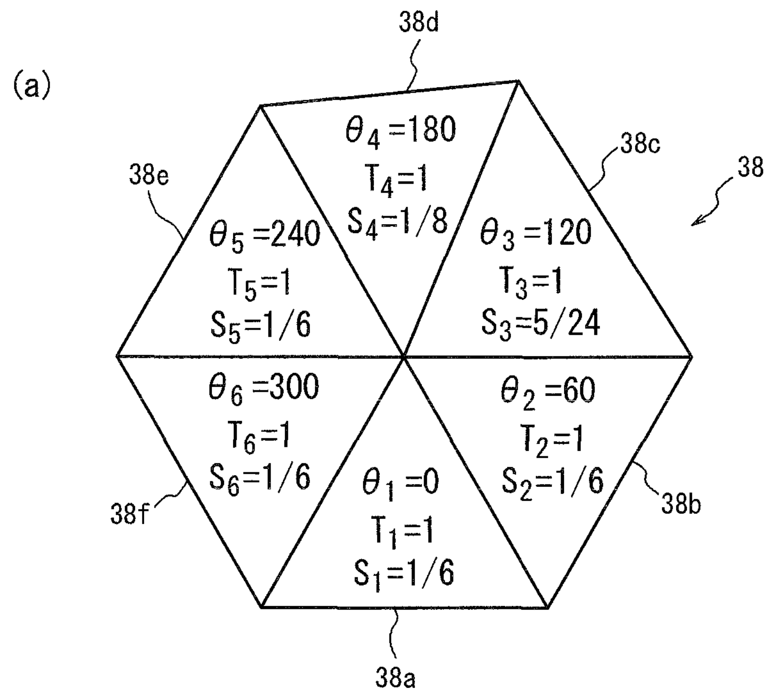
FIG. 17 is a diagram illustrating an exemplary variant of a modulation state of the modulation optical element according to the present invention.
Figure 17:
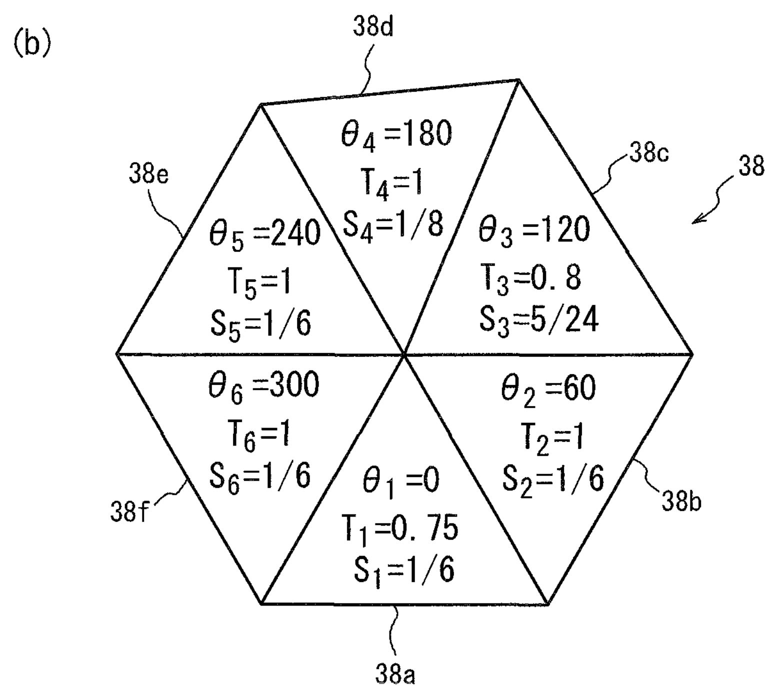

It is assumed that, for example, the modulation optical element 38 is divided into 6 optical multilayer regions 38*a*-38*f* about the optical axis as shown in FIG. 17(*a*) and the dimensions of the optical multilayer regions 38*c* and 38*d* are different from those of the other optical multilayer regions. In this case, the transmittances of the optical multilayer regions 38*a*, 38*c* are adjusted by the adjustment element, in order as to satisfy the formula (1), as shown in FIG. 17(*b*).

Figure 18:
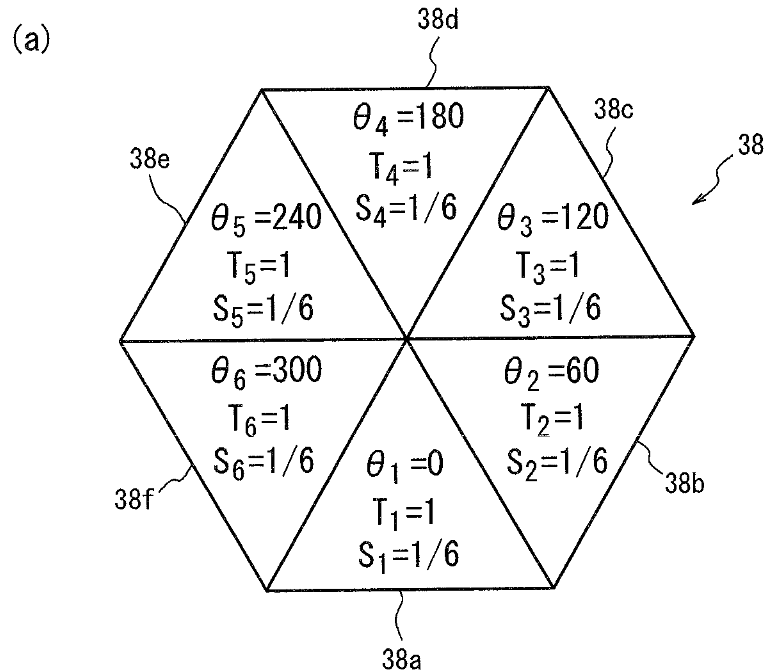
FIG. 18 is a diagram illustrating another exemplary variant of the modulation state of the modulation optical element according to the present invention.
Figure 18:
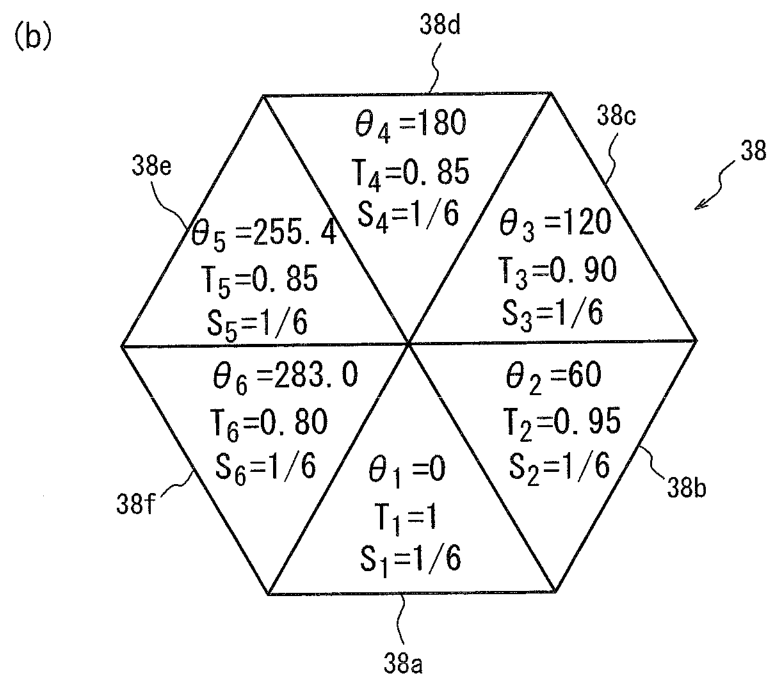
Figure 19:
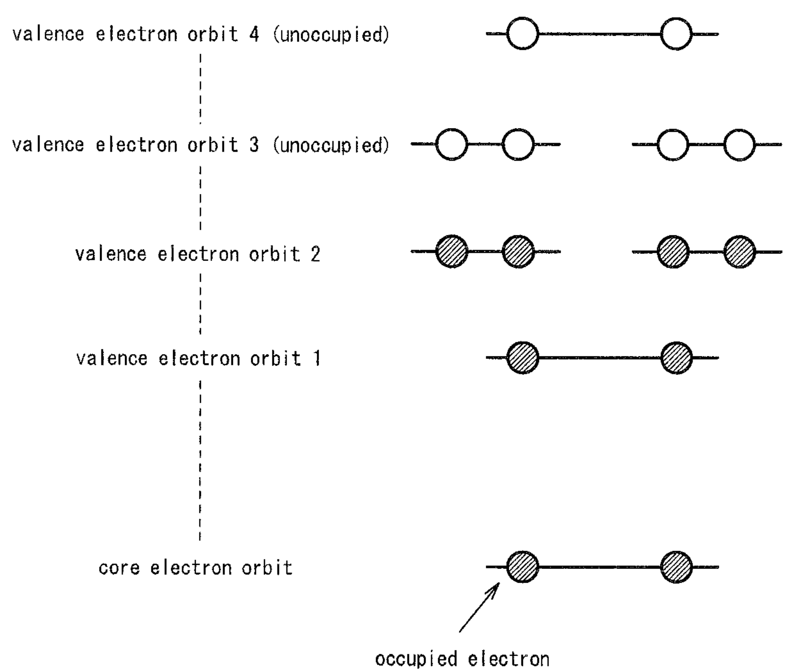
FIG. 19 is a conceptual diagram illustrating an electronic configuration of a valence electron trajectory of a molecule composing a sample.
Figure 20:
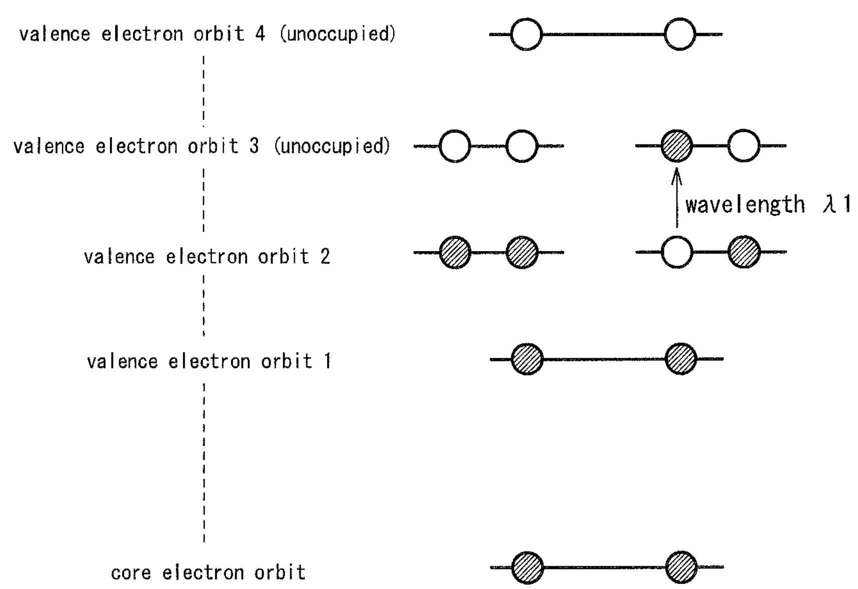
FIG. 20 is a conceptual diagram illustrating a first excited state of the molecules shown in FIG. 19.
Figure 21:
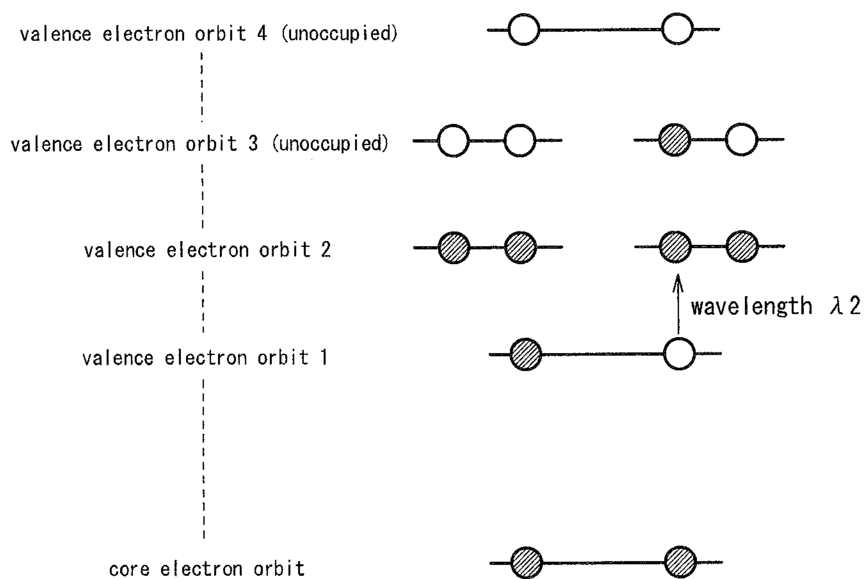
FIG. 21 is a conceptual diagram illustrating a second excited state of the molecules shown in FIG. 19.
Figure 22:
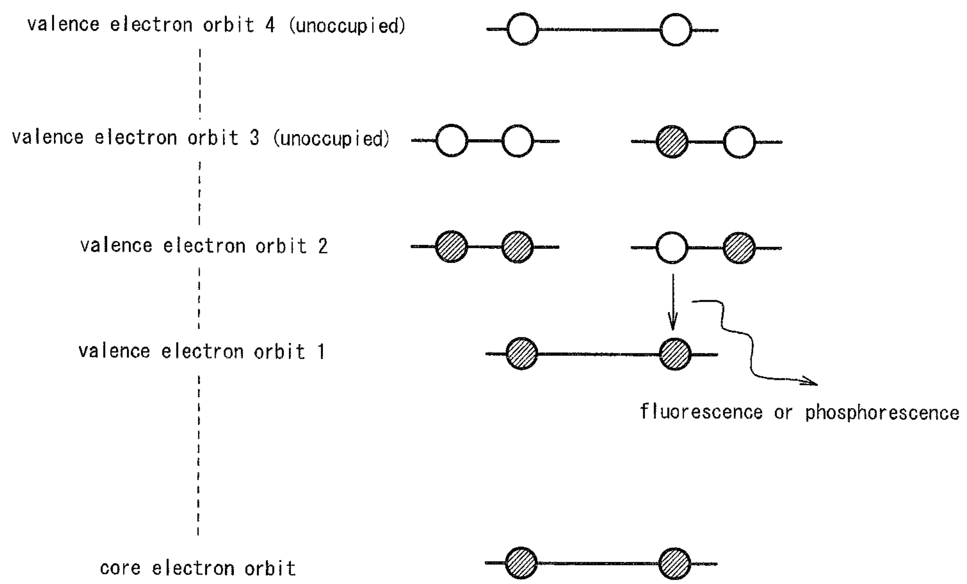
FIG. 22 is a conceptual diagram illustrating a state in which the molecules shown in FIG. 19 return from the second excited state to the ground state.
Figure 23:
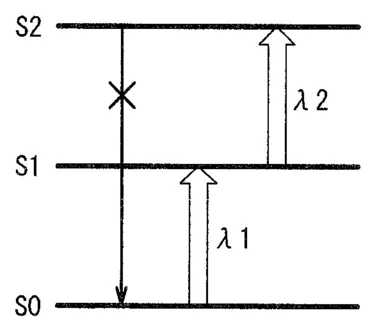
FIG. 23 is a conceptual diagram illustrating a double resonance absorption process of the molecule.
Figure 24:
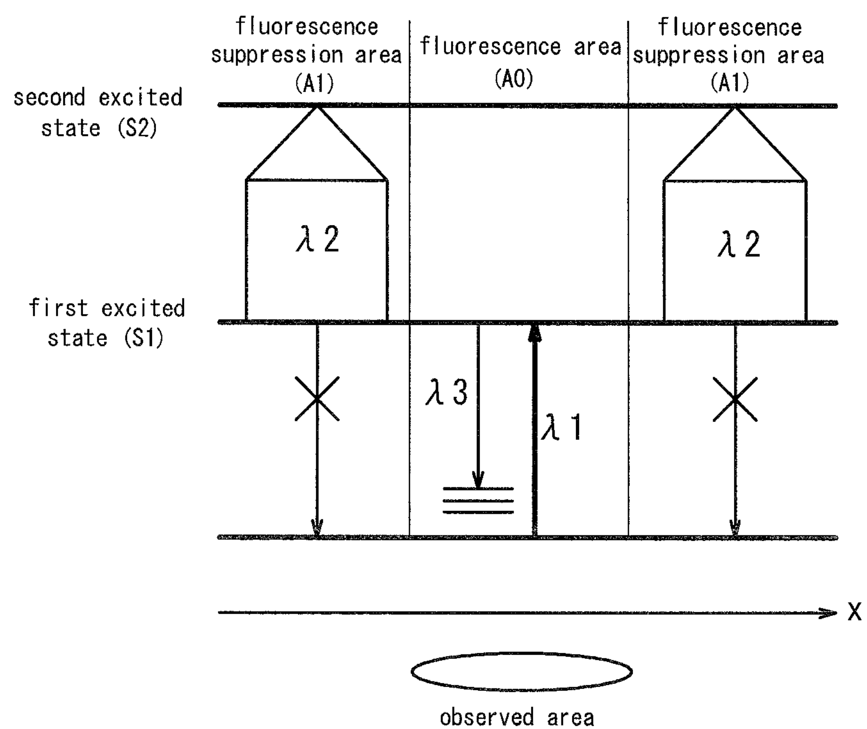
FIG. 24 is a conceptual diagram illustrating the double resonance absorption process of the molecule.

In addition, there may be a case in which, with the modulation optical element 38 manufactured in conformity with the design values as shown in FIG. 18(*a*), the formula (1) is not satisfied because of an absorption effect of the erasing light and the like generated in another part of the microscopic optical system. In this case, as shown in FIG. 18(*b*), for example, the transmittances of the optical multilayer regions 38*b*, 38*c*, 38*d* are adjusted by the adjustment element, while the phases and the transmittances of the optical multilayer regions 38*e*, 38*f* are adjusted by the adjustment element, in order to satisfy the formula (1). In using the modulation optical element 38 shown in FIG. 17(*b*) and FIG. 18(*b*), the iris 37 may either be omitted or used to finely adjust the property of the erasing light after having transmitted through the modulation optical element 38.

In addition, the configuration according to the third embodiment is applicable not only to the ultra-high resolution microscope of the fluorescence suppression type but to an infrared ultra-high resolution microscopy for coaxially irradiating the infrared light and a hollow visible light (for example, Bokor. et. al OPTICS COMMUNICATIONS, 283 (2010) 509). Moreover, according to the third embodiment, it is also possible to configure, by using at least two tunable lasers such as a laser beam source of light parametric emission, Ti sapphire laser, supercontinuum laser and the like in place of a plurality of single-color emission laser beam sources, in order to handle a variety of combinations of the wavelengths.

Furthermore, although the ultra-high resolution microscope adopting the two-color light source is exemplified in the above embodiments, the present invention is also applicable to the microscopic system adopting three- or more-color light sources (for example, S Hell. et. al J. Microscopy 236 (2009)35) and thus much more versatile.

REFERENCE SIGNS LIST

| | |
|---|---|
| 1 | modulation optical element |
| 2 | transmittance compensation plate |
| 10 | modulation optical element |
| 11 | center region |
| 20 | Fresnel zone plate |
| 21 | transmittance compensation plate |
| 31 | pumping light source |
| 32 | erasing light source |
| 34 | reflector |
| 35 | dichroic mirror |
| 37 | iris |
| 38 | modulation optical element |
| 39 | beam splitter |
| 40 | microscope objective lens |
| 41 | sample stage |
| 42 | sample |
| 43 | spectroscope |
| 44 | photodetector |
| 50 | modulation optical element |
| 60 | collective lens |

-continued

REFERENCE SIGNS LIST

| | |
|---|---|
| 61 | single mode fiber |
| 62 | collimator lens |
| 63 | galvano scanning unit |
| 64 | pupil projection lens |
| 71, 72, 73, 74, 75 | laser beam source |
| 86, 91 | rotary ND filter |
| 92, 93 | acousto-optical wavelength-tunable filter |
| 96 | confocal pinhole |
| 97 | filter unit |
| 101, 102 | rotary filter |
| 111x, 111y | drive unit |
| 112 | control unit |

The invention claimed is:

1. A microscope comprising:

an illumination light source unit capable of generating illumination light;

an adjustment element for adjusting an optical property of the illumination light;

a modulation optical element having a plurality of regions for spatial modulation of the illumination light;

an illumination optical system including an objective lens for collecting the first illumination light and the second illumination light on a sample including the material by partially overlapping the lights;

a photodetector for detecting emitted light from the sample as irradiated with the first illumination light and the second illumination light from the illumination optical system;

a confocal pinhole having an aperture of variable size, disposed in a position conjugate with a focal position of the objective lens on an incidence side of the photodetector;

a drive unit for varying the size of the aperture of the confocal pinhole; and a control unit for simultaneously generating the first illumination light and the second illumination light by controlling the plurality of illumination light sources and also for controlling the aperture of the confocal pinhole, via the drive unit, in order to satisfy the following formula in accordance with the first illumination light and the second illumination light $$0.61\frac{\lambda_p}{NA}M > a \geq 0.49\sqrt{\frac{\varepsilon_e}{\tau\sigma_{dip}C_{e0}}}\frac{\lambda_e}{NA}M$$

NA: numerical aperture of objective lens

M: magnification of photodetector for focusing image on object side

λp: wavelength of first illumination light

λe: wavelength of second illumination light $\sigma_{dip}$: fluorescence suppressing cross-section area $C_{e0}$: peak intensity of second illumination light $\epsilon_e$: photon flux of second illumination light, wherein the illumination light has a first illumination light for making a material having at least two excited quantum states emit light by exciting the material from a stable state to a first quantum state, and a second illumination light for suppressing emission of light by making the material further transit to another quantum state, wherein the modulation optical element and the adjustment element are disposed in the illumination optical system.

2. The microscope according to claim 1, wherein the adjustment element adjusts the illumination light having passed through the modulation optical element such that an unsymmetrical component of at least one of a transmittance and a phase around an optical axis is cancelled out between the plurality of regions of the modulation optical element.

3. The microscope according to claim 1, wherein the adjustment element adjusts such that the following relation expression is satisfied, provided that $S_i$ represents dimensions of each region i corresponding to the plurality of regions on a pupil plane of the illumination light spatially modulated by the modulation optical element, $\theta_i$ represents a phase of a light having passed through an area corresponding to each region i, $T_i$ represents the transmittance, and $U_i$ represents an energy density, $$\sum_{i=1}^{n} T_i S_i \sin\theta_i = \sum_{i=1}^{n} U_i = 0.$$

4. The microscope according to claim 1, wherein the adjustment element is integrally formed in the modulation optical element.

5. The microscope according to claim 1, wherein the modulation optical element includes regions radially divided about the optical axis as the plurality of regions.

6. The microscope according to claim 5, wherein the following equation $T_a S_a \sin\theta_a + T_b S_b \sin\theta_b = 0$ is satisfied, provided that, for the plurality of regions of the modulation optical element, a region a has a transmittance $T_a$, dimensions $S_a$ and a phase $\theta_a$, whereas a region b, located across the optical axis from the region a, has a transmittance $T_b$, dimensions $S_b$ and a phase $\theta_b$.

7. The microscope according to claim 6, wherein the region a and the region b are in the same size.

8. The microscope according to claim 1, wherein the plurality of regions of the modulation optical element are concentrically divided around a central axis of the modulation optical element.

9. The microscope according to claim 1, wherein the modulation optical element modulates a phase of the second illumination light.

10. The microscope according to claim 9, wherein the modulation optical element makes the first illumination light transmit without changing a sign of an electric field.

11. The microscope according to claim 10, wherein the modulation optical element has optical multilayer.

12. The microscope according to claim 1, wherein the illumination optical system overlaps an optical axis of the first illumination light and an optical axis of the second illumination light in a spatially matching manner.

13. The microscope according to claim 12, wherein the illumination optical system has a single mode fiber, and the first illumination light and the second illumination light are incident on the modulation optical element and the adjustment element via the single mode fiber.

14. The microscope according to claim 1, wherein the adjustment element comprises an iris for adjusting a diameter of luminous flux of the illumination light.

15. The microscope according to claim 14, wherein the iris is movable in a direction orthogonal to the optical axis of the illumination light entering.

16. The microscope according to claim 1, comprising a plurality of illumination light sources capable of generating illumination lights, wherein the first illumination light and the second illumination light are simultaneously generated from the plurality of illumination light sources.

17. A microscope comprising:

an adjustment element for adjusting an optical property of an illumination light; and a modulation optical element having a plurality of regions for spatial modulation of the illumination light, wherein the adjustment element adjusts such that the following relation expression is satisfied, provided that $S_i$ represents dimensions of each region i corresponding to the plurality of regions on a pupil plane of the illumination light spatially modulated by the modulation optical element, $\theta_i$ represents a phase of a light having passed through an area corresponding to each region i, $T_i$ represents the transmittance, and $U_i$ represents an energy density, $$\sum_{i=1}^{n} T_i S_i \sin\theta_i = \sum_{i=1}^{n} U_i = 0.$$

* * * * *